(12) United States Patent
Shin et al.

(10) Patent No.: US 12,296,024 B2
(45) Date of Patent: May 13, 2025

(54) MODIFIED ZINC OXIDE NANOCOMPOSITE, ANTIBIOTIC COMPOSITION COMPRISING THE SAME, AND COMBINATION PREPARATION WITH THE SAME

(71) Applicant: UIF (University Industry Foundation), Yonsei University, Seoul (KR)

(72) Inventors: Yong Shin, Seoul (KR); Huifang Liu, Seoul (KR)

(73) Assignee: UIF (UNIVERSITY INDUSTRY FOUNDATION), YONSEI UNIVERSITY, Seoul (KR)

( * ) Notice: Subject to any disclaimer, the term of this patent is extended or adjusted under 35 U.S.C. 154(b) by 425 days.

(21) Appl. No.: 17/859,724

(22) Filed: Jul. 7, 2022

(65) Prior Publication Data
US 2023/0027034 A1    Jan. 26, 2023

(30) Foreign Application Priority Data
Jul. 9, 2021 (KR) .................. 10-2021-0090179

(51) Int. Cl.
*A61K 31/496* (2006.01)
*A61K 31/7048* (2006.01)
(Continued)

(52) U.S. Cl.
CPC ........ *A61K 47/6929* (2017.08); *A61K 31/496* (2013.01); *A61K 31/7048* (2013.01);
(Continued)

(58) Field of Classification Search
CPC .............. A61K 47/6929; A61K 31/496; A61K 31/7048; A61K 33/30; A61K 47/6923; A61P 31/04; A61P 31/10; C01G 9/00
See application file for complete search history.

(56) References Cited

U.S. PATENT DOCUMENTS

| | | | |
|---|---|---|---|
| 10,105,875 B2* | 10/2018 | Young | B29C 59/022 |
| 2010/0172993 A1* | 7/2010 | Singh | A61K 9/19 |
| | | | 564/387 |
| 2018/0289600 A1* | 10/2018 | Suma | A61K 8/0241 |

FOREIGN PATENT DOCUMENTS

| | | |
|---|---|---|
| KR | 10-2011-0079623 A | 7/2011 |
| KR | 10-2019-0117358 A | 10/2019 |
| KR | 10-2136696 B1 | 7/2020 |

OTHER PUBLICATIONS

Liu, Huifang et al. "Facile Homobifunctional Imidoester Modification of Advanced Nanomaterials for Enhanced Antibiotic Synergistic Effect" ACS Appl. Mater. Interfaces (2021) 13, 40401-40414. (Year: 2021).*

(Continued)

*Primary Examiner* — Joseph K McKane
*Assistant Examiner* — Jalisa Holmes Ferguson
(74) *Attorney, Agent, or Firm* — Paratus Law Group, PLLC

(57) ABSTRACT

A zinc oxide nanocomposition is modified with a homobifunctional imidoester compound and an antibiotic composition contains the zinc oxide nanocomposition as an active ingredient. Also, a combination preparation contains the zinc oxide nanocomposite and an antifungal agent. The zinc oxide nanocomposite provides an antibiotic composition which is less toxic while exhibiting excellent antibiotic activity, for example, antiviral, antibacterial or antifungal activity. The antibiotic composition is usable to prevent contamination or infection by viruses, bacteria or fungi, inhibit the growth of viruses, bacteria or fungi, or treat infections by viruses, bacteria or fungi.

16 Claims, 30 Drawing Sheets

(51) Int. Cl.
    *A61K 33/30*     (2006.01)
    *A61K 47/69*     (2017.01)
    *A61P 31/04*     (2006.01)
    *A61P 31/10*     (2006.01)
    *C01G 9/02*     (2006.01)

(52) U.S. Cl.
    CPC .......... *A61K 33/30* (2013.01); *A61K 47/6923* (2017.08); *A61P 31/04* (2018.01); *A61P 31/10* (2018.01); *C01G 9/02* (2013.01)

(56) References Cited

OTHER PUBLICATIONS

Sirelkhatim et al. "Review on Zinc Oxide Nanoparticles: Antibacterial Activity and Toxicity Mechanism" Nano-Micro Lett. (2015) 7(3) 219-242. (Year: 2015).*

Mallakpour et al. "Effect of modified ZnO capped with N-trimeillitylimido-L-alanine diacid as an optically active coupling agent on the morphology and thermal properties of poly (amide-imide)/ZnO nanocomposites" (2015) Designed Monomers and Polymers, 18(1), 79-88. (Year: 2015).*

Alshahrie, Ahmed et al. "Structure, magnetic and optical behaviors of Zn1-xCoxO (0.01-x-0.09) films developed by DMP modified sol-gel spin-coating technique" Superlattices and Microstructures, (2018) 124, 192-200 (Year: 2018).*

Aiping Hui et al., "Hydrothermal Fabrication of Spindle-Shaped ZnO/Palygorskite Nanocomposites Using Nonionic Surfactant for Enhancement of Antibacterial Activity", Nanomaterials, Oct. 13, 2019, pp. 1-13.

Linlin Zhong et al., "Synthesis of ZnO nanoparticles-decorated spindle-shaped graphene oxide for application in synergistic antibacterial activity", Journal of Photochemistry and Photobiology B: Biology, May 3, 2018, pp. 293-301, vol. 183.

Amna Sirelkhatim et al., "Review on Zinc Oxide Nanoparticles: Antibacterial Activity and Toxicity Mechanism", Nano-Micro Lett., Apr. 19, 2015, pp. 219-242.

Korean Office Action for related KR Application No. 10-2021-0090179 mailed Oct. 17, 2022 from Korean Intellectual Property Office.

* cited by examiner

MODIFIED ZINC OXIDE NANOCOMPOSITE, ANTIBIOTIC COMPOSITION COMPRISING THE SAME, AND COMBINATION PREPARATION WITH THE SAME

CROSS-REFERENCE TO RELATED APPLICATION

This application claims priority to and the benefit of Korean Patent Application No. 10-2021-0090179, filed on Jul. 9, 2021, the disclosure of which is incorporated herein by reference in its entirety.

BACKGROUND

The present invention relates to a modified zinc oxide nanocomposite, an antibiotic composition containing the same, and a combination preparation with the same.

Antibiotic resistance due to misuse and abuse of antibiotics is a major public health threat worldwide. In particular, infections caused by multi-drug resistant bacteria (super bacteria), fungi, gram-negative bacteria, or methicillin-resistant *S. aureus* (MRSA) are difficult to treat due to resistance to numerous antibiotics. Further, since mold infection weakens the patient's immune system, it causes increased mortality for cancer patients and organ transplant patients. Therefore, it is important to develop a new strategy for finding a new treatment for microbial infections.

Meanwhile, one of the other problems with the use of existing antibiotics is that blood clots are caused by increasing the viscosity of blood. Accordingly, the nanopharmaceutical industry has recently made a lot of efforts to find ways to prevent coagulation in the bloodstream, especially blood coagulation after intravenous injection.

Accordingly, there is a need for developing an antibiotic material that not only exhibits excellent antibiotic effects but can also be used as an injection.

SUMMARY

An object of the present invention is to provide an antibiotic material that can be used as an injection while exhibiting excellent antibiotic activity.

Another object of the present invention is to provide an antibiotic composition containing the above-described antibiotic material as an active ingredient.

Still another object of the present invention is to provide a composition that can be used with existing antibiotics, for example, antiviral agents, antibacterial agents, or antifungal agents and can improve the efficacy of these antibiotics.

According to an aspect of the present invention, provided is a zinc oxide nanocomposite modified with a compound represented by the following Chemical Formula 1:

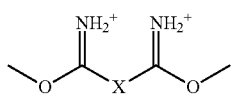

[Chemical Formula 1]

In Chemical Formula 1, X is $(CH_2)_n$, and n is an integer from 5 to 10.

According to another aspect of the present invention, provided is an antibiotic composition containing the above-described zinc oxide nanocomposite as an active ingredient.

According to still another aspect of the present invention, provided is an antifungal combination preparation containing the above-described zinc oxide nanocomposite and an antifungal agent.

The zinc oxide nanocomposite according to the present invention may provide an antibiotic composition which is less toxic while exhibiting excellent antibiotic activity, for example, antiviral, antibacterial or antifungal activity. Accordingly, the antibiotic composition may be used to prevent contamination or infection by viruses, bacteria or molds, inhibit the growth of viruses, bacteria or molds, or treat infections by viruses, bacteria or molds. In addition, when the antibiotic composition is used in combination with an existing antifungal agent, a synergistic effect is exhibited by improving the efficacy of the antifungal agent. Therefore, the antibiotic composition can be used as an excellent antifungal combination preparation, and enables the use of a low dose of an existing antifungal agent to reduce side effects due to toxicity.

BRIEF DESCRIPTION OF THE DRAWINGS

FIG. 6A illustrates *Aspergillus* colonies cultured for 7 days using ZnO nanomaterials at 0.6 mg/mL, and FIG. 6B is a graph showing the proportion of *Aspergillus* colonies according to the concentration when various concentrations (0.1 to 1.0 mg/mL) of ZnO nanomaterials were used;

FIG. 7A illustrates the *Aspergillus* colonies observed on day 4 of culture of ZnO nanomaterials. FIG. 7B is a graph showing the growth rate of *Aspergillus* colonies observed during the 10-day culture;

FIG. 11A illustrates the change in body weight of male mice, and FIG. 11B illustrates the change in body weight of female mice. FIGS. 11C and 11D illustrate changes in mouse kidney (FIG. 11C) and liver (FIG. 11D) weights 14 days after intravenous administration of a low-dose (LD) and high-dose (HD) of NS—ZnO or the HINS composite. The amounts of total protein (TP) and albumin in the blood are illustrated in FIG. 11E, and the amounts of cholesterol (T-Chol) and triglyceride (TG) are illustrated in FIG. 11F, after euthanizing the mice.

DETAILED DESCRIPTION

Figure 1:
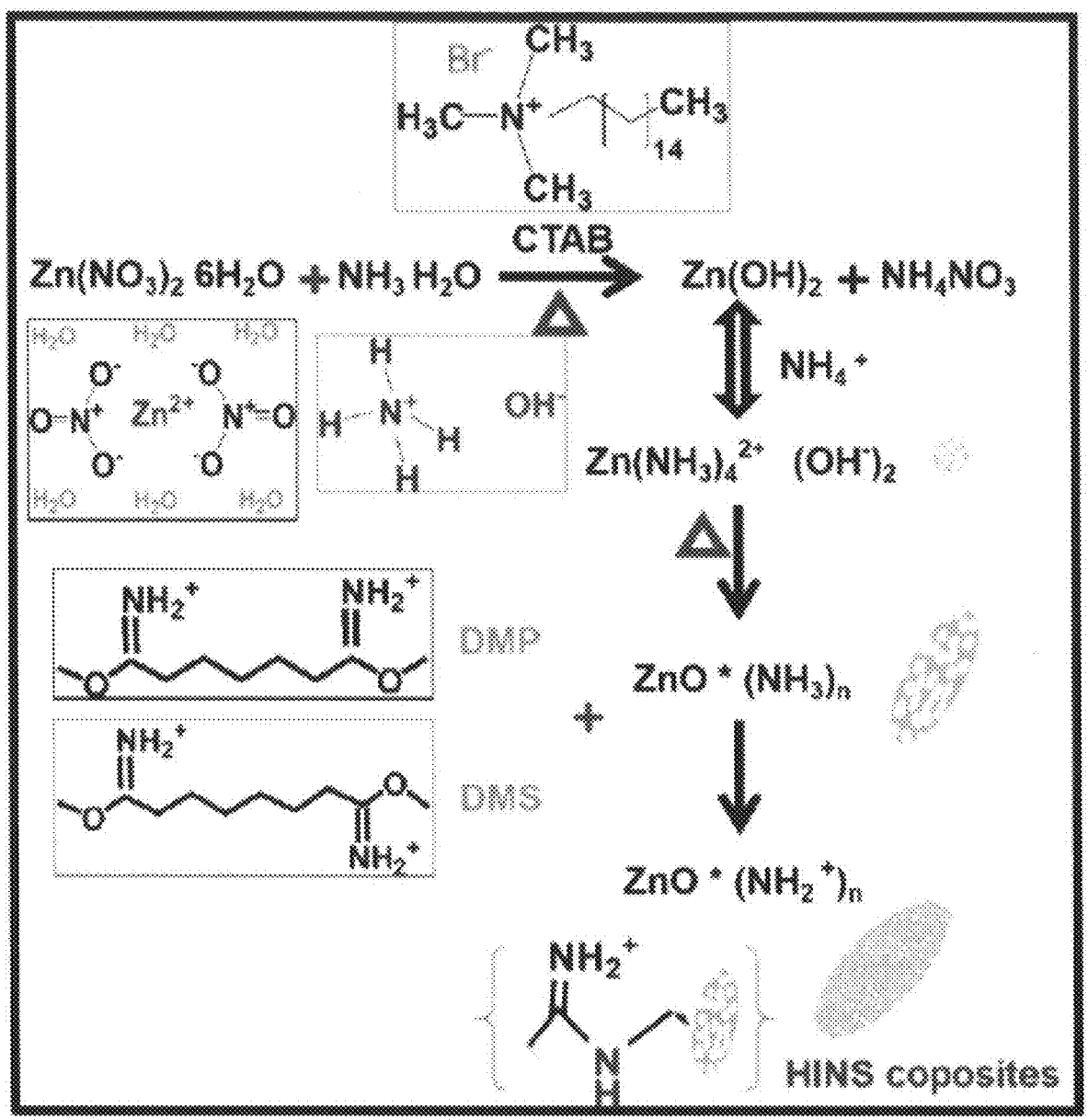
FIG. 1 is a view schematically illustrating the structure and synthesis method of HINS composites.

Hereinafter, the present invention will be described in detail.

The terms used in the present application are used only to describe specific embodiments, and are not intended to limit the present invention. Unless defined otherwise, all terms used herein, including technical or scientific terms, have the same meaning as commonly understood by a person with ordinary skill in the art to which the present invention pertains.

Throughout the specification, when a part "includes", "contains" and "has" a constituent element, it means that other constituent elements may be further included unless otherwise specifically defined.

According to an aspect of the present invention, provided is a zinc oxide nanocomposite modified with a compound represented by the following Chemical Formula 1:

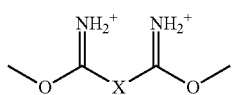

[Chemical Formula 1]

In Chemical Formula 1, X is $(CH_2)_n$, and n is an integer from 5 to 10.

The compound represented by Chemical Formula 1 may be a homobifunctional imidoester compound. As the homobifunctional imidoester compound represented by Chemical Formula 1, dimethyl adipimidate, dimethyl pimelimidate, dimethyl suberimidate, and 3,3'-dithiobispropionimidate may be included. Thus, according to an exemplary embodiment of the present invention, a zinc oxide nanocomposite modified with dimethyl adipimidate, dimethyl pimelimidate, dimethyl suberimidate, or 3,3'-dithiobispropionimidate, for example, dimethyl pimelimidate or dimethyl suberimidate may be provided. The compounds may cross a surface energy barrier and may sufficiently add an amine group capable of activating the zinc oxide bandgap to the surface of zinc oxide nanocrystal.

In the present invention, the modification of the zinc oxide nanocomposite modified with the compound represented by Chemical Formula 1 may be obtained by mixing a salt of the compound represented by Chemical Formula 1 with zinc oxide nanocrystals. Specifically, the zinc oxide nanocomposite may be prepared by a step of preparing zinc oxide nanocrystals and a step of mixing the prepared zinc oxide nanocrystals with a salt of the compound represented by Chemical Formula 1, for example, an HCl salt. Here, the zinc oxide nanocrystals may be prepared by hydrothermal synthesis, for example, the hydrothermal synthesis may be performed by heating a zinc precursor along with water at 85 to 95° C. for 30 to 85 minutes, and in this case, the zinc precursor may be heated along with a surfactant such as hexadecyltrimethylammonium bromide.

The zinc oxide nanocrystals for the zinc oxide nanocomposite of the present invention may be in the form of nano-sized crystals. According to an exemplary embodiment of the present invention, the zinc oxide nanocrystals may be nanocrystals having a size of 100 to 300 nm, for example 130 to 230 nm. Further, according to an exemplary embodiment of the present invention, the zinc oxide nanocrystals may be in the form of spherical particles or in the form of a spindle. The spindle form refers to a form in which both ends are pointed and a central portion is convex, and may be, for example, the form illustrated in FIG. 2A of the present specification. According to another exemplary embodiment of the present invention, the zinc oxide nanocomposite of the present invention in which the zinc oxide nanocrystals are modified with the compound of Chemical Formula 1 may also have a spherical particle or spindle form. The spindle form has an advantage of increasing the flow rate of the zinc oxide nanocomposite in blood, which reduces the likelihood of aggregation in an injection therapy such as intravenous injection. In addition, the sharp ends of the spindle form may help destroy the cell walls of microorganisms such as viruses, bacteria, and fungi, and thus may also contribute to an increase in the antibiotic effect. Therefore, it is preferred that the zinc oxide nanocomposite has a spindle form.

According to an exemplary embodiment of the present invention, the zinc oxide nanocomposite of the present invention may have a positive surface charge. As the composite exhibits a positive charge as described above, it is possible to exhibit an effect of attracting microorganisms such as viruses, bacteria or fungi.

According to another exemplary embodiment of the present invention, an antibiotic composition containing the above-described zinc oxide nanocomposite as an active ingredient. As used herein, the term "antibiotic composition" refers to a composition containing antibiotics that kill microorganisms or suppress the growth of microorganisms, the microorganisms including viruses, fungi, protozoa and bacteria. Accordingly, the antibiotic has antibiotic activity, that is, antiviral activity, antibacterial activity, or antifungal activity. Thus, according to an exemplary embodiment of the present invention, the antibiotic composition of the present invention may be a composition having antiviral activity, antibacterial activity, or antifungal activity.

According to an exemplary embodiment of the present invention, the antibiotic composition according to the present invention may have antibacterial activity against Gram-negative bacteria. The composite according to the present invention is an effective ingredient for preventing bacterial contamination or infection, inhibiting bacterial growth, or treating bacterial infection. Examples of the gram-negative bacteria include *Escherichia coli, Salmonella, Shigella,* Typhus, *Vibrio cholerae, Neisseria gonorrhoeae, Neisseria meningitidis,* and the like. According to an exemplary embodiment of the present invention, the composition of the present invention may have antibacterial activity against *Escherichia coli* or *Salmonella*.

According to an exemplary embodiment of the present invention, the antibiotic composition according to the present invention may have antifungal activity. The composite according to the present invention is an effective ingredient for preventing mold contamination or infection, inhibiting mold growth, or treating mold infection. The composition having the antifungal activity according to the present invention may exhibit antifungal activity against pathogenic fungi, for example *Candida albicans, Cryptococcus neoformans, Candida glabrata, Candida lusitaniae, Candida tropicalis, Aspergillus niger, Aspergillus fumigatus, Fusarium oxysporum, Saccharomyces cerevisiae* and the like. According to an exemplary embodiment of the present invention, the composition of the present invention may have antifungal activity against fungi of the genus *Aspergillus*.

Further, according to another aspect of the present invention, a pharmaceutical composition for preventing or treating viral infections, bacterial infections, or fungal infections, containing a zinc oxide nanocomposite modified with the compound represented by Chemical Formula 1 as an active ingredient, may be provided.

According to an exemplary embodiment of the present invention, the antibiotic composition according to the present invention may be used with an additional antifungal agent. In addition, according to still another aspect of the present invention, provided is an antifungal combination preparation containing the above-described zinc oxide nanocomposite and an antifungal agent. The antifungal agent used with the antibiotic composition according to the present invention or the antifungal agent included in the combination preparation along with the zinc oxide nanocomposite according to the present invention may be, for example, one or more selected from the group consisting of ketoconazole, itraconazole, fluconazole, miconazole, clotrimazole, fenticonazole, econazole, bifonazole, oxiconazole, chloconazole, roll cyclate, amphotericin B, flucytosine, griseofulvin, terbinafine, nystatin, tolnaftate, naftifine, haloprogin, ciclopirox, triclosan, noprosacsin, ciprosacsin and salts. According to an exemplary embodiment of the present invention, the antifungal agent may be itraconazole or amphotericin B. Specifically, the antibiotic composition containing the zinc oxide nanocomposite according to the present invention may be administered simultaneously or at different times from when itraconazole or amphotericin B is administered, or may be administered by formulating the zinc oxide nanocomposite according to the present invention into a combination preparation with itraconazole or amphotericin B.

The above-described antibiotic composition, pharmaceutical composition or combination preparation of the present invention may further include a pharmaceutically acceptable carrier. The pharmaceutically acceptable carrier may be typically used in the field of pharmaceuticals and may be an excipient (for example, starch, calcium carbonate, sucrose, lactose, sorbitol, mannitol, cellulose, and the like) or a diluent (for example, physiological saline, purified water, and the like).

Further, if necessary, the antibiotic composition, pharmaceutical composition or combination preparation of the present invention may further include a pharmaceutically acceptable additive other than the pharmaceutically acceptable carrier, for example, a binder, a disintegrant, a lubricant, a coating agent, a film coating agent, an enteric film coating agent, a soft capsule agent, a solubilizing agent, an emulsifier, a suspending agent, a stabilizer, a buffer, an antioxidant, a surfactant, a sweetening agent, a flavoring agent, a preservative, a thickening agent, an aroma, or a colorant.

The antibiotic composition, pharmaceutical composition, or combination preparation of the present invention may be administered orally or parenterally. In the case of parenteral administration, the antibiotic composition, pharmaceutical composition, or combination preparation of the present invention may be administered by intravenous injection, subcutaneous injection, intramuscular injection, peritoneal injection, endothelial administration, local administration, intranasal administration, intrapulmonary administration, rectal administration, or the like. For oral administration, the pharmaceutical composition of the present invention may be formulated in the form of a solid formulation. In the case of a liquid preparation, the active ingredient may be formulated together with a carrier such as purified water and physiological saline, and if necessary, a solubilizing agent such as sucrose monostearate, a stabilizer such as polyvinylpyrrolidone, and the like.

According to an exemplary embodiment of the present invention, the antibiotic composition, pharmaceutical composition, or the combination preparation of the present invention may be used for injection, for example, intravenous injection.

The dose of the antibiotic composition, pharmaceutical composition, or combination preparation of the present invention may be determined in consideration of the method of administration, the age and sex of the medicine taker, the severity of the patient, the status, inactivation rate, and the type of drug used in combination, and may be administered in a single dose or in several divided doses.

Meanwhile, the composition according to the present invention does not necessarily need to be administered to humans or non-human animals, and may be combined with an appropriate diluent, and the like and thus used after being formulated into a form to be sprayed or applied to a required place or device for the purpose of preventing contamination by fungi or bacteria or inhibiting their reproduction.

Hereinafter, the present invention will be described in more detail with reference to exemplary embodiments of the present invention. Since the exemplary embodiments are presented for the purpose of describing the present invention, the present is not limited thereto.

Synthesis Examples (1) Preparation of ZnO Nanospindle (NS) Crystals

ZnO NS crystals were synthesized in an alkaline medium by a hydrothermal synthesis method. Briefly, 1 mL of 1 M $Zn(NO_3)_2 \cdot 6H_2O$ (Sigma, 228737-100G) and 1 mL of 1 M cetyltrimethylammonium bromide (CTAB, DaeJung Chemicals, 2544-4105) were added to 98 mL of Milli-Q water in a 250-mL flask, and stirred with a magnetic bar while being heated at 95° C. for 50 minutes (500 rpm). Thereafter, 2 mL of an ammonium hydroxide solution (DaeJung Chemicals, 1065-3300) was added dropwise to the reaction mixture under stable stirring conditions. Stirring resulted in a milky colloidal solution. The reaction flask was immediately placed in a freezer at 0° C. to stop the growth of ZnO NS.

After about 10 minutes, the mixture was transferred to a 50 mL tube and centrifuged. Thereafter, the supernatant was removed and the precipitate was resuspended with Milli-Q water to wash away the remaining ions (repeated three times). Finally, the precipitate was dried at 56° C. in a drying oven (Yamato, DX312C) overnight.

Figure 2A:
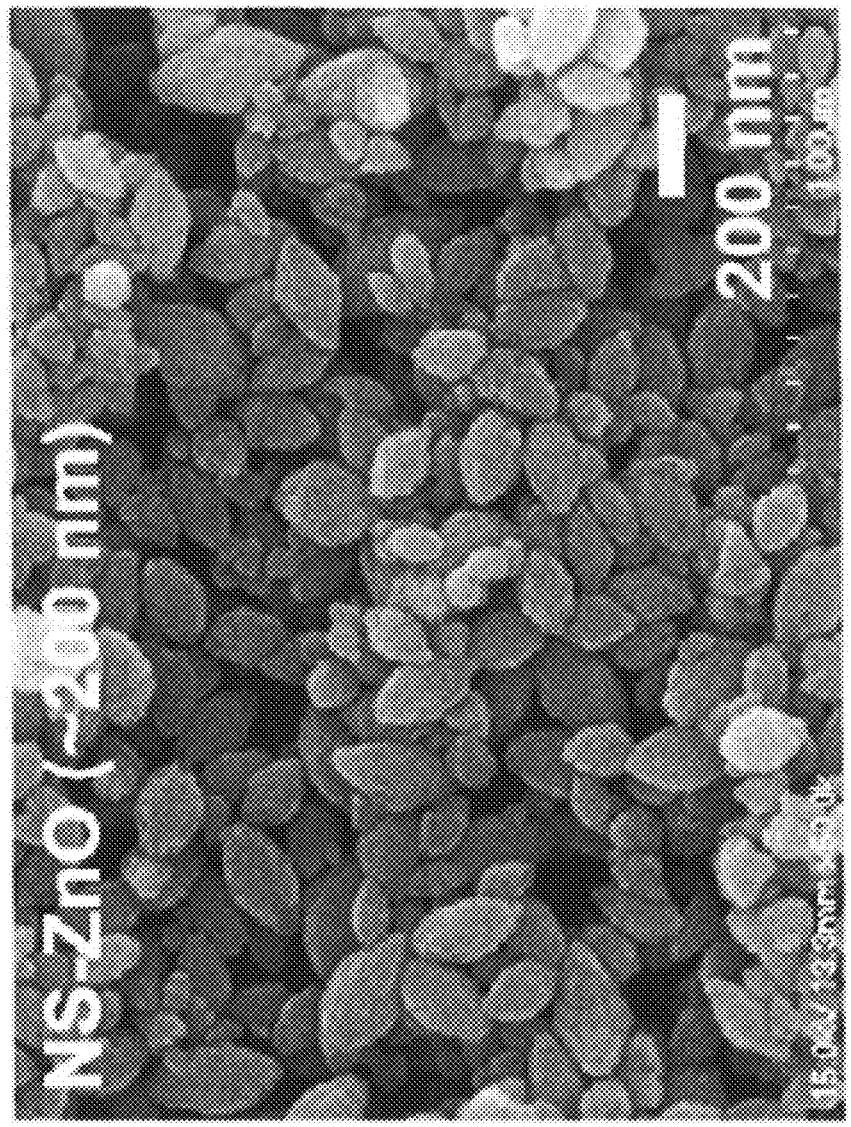
FIG. 2A is an SEM image of NS—ZnO (approximately 200 nm) synthesized with a uniform nanospindle structure.
Figure 2B:
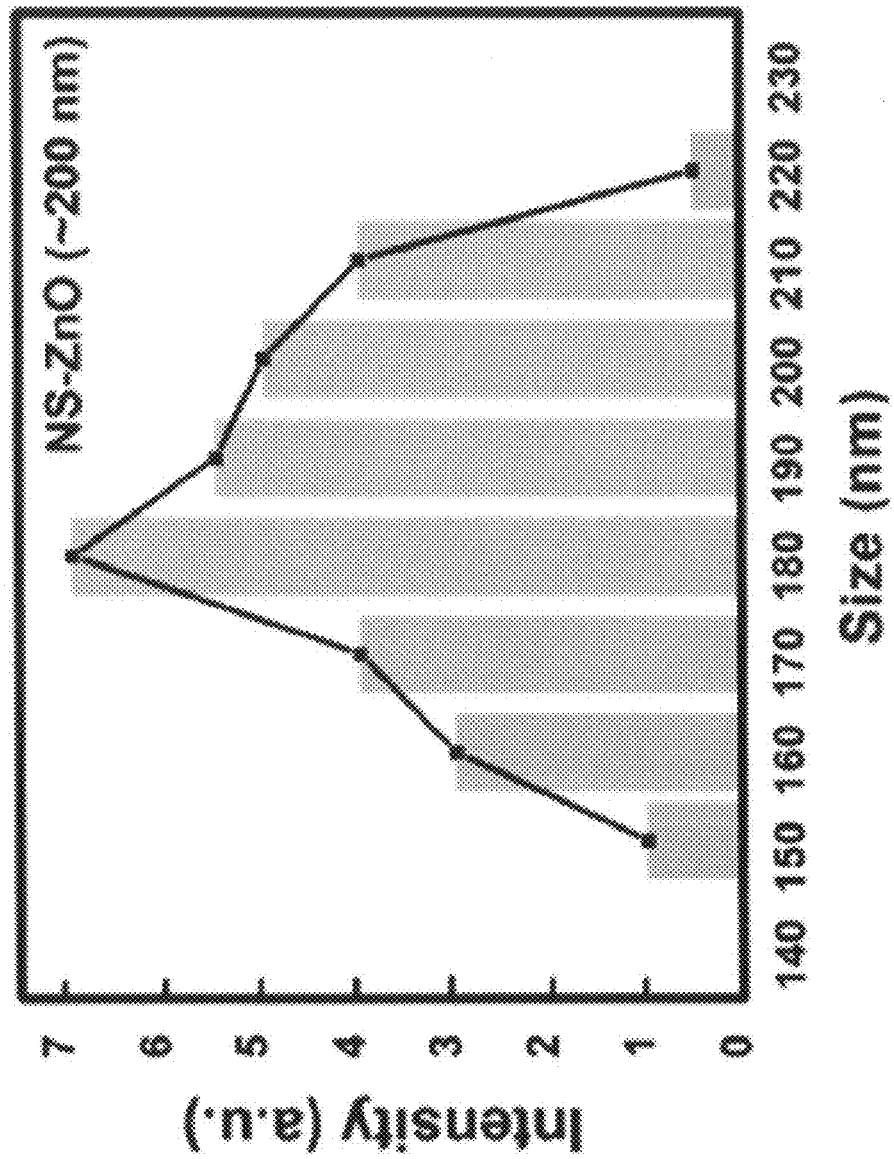
FIG. 2B is a dynamic light scattering (DLS) analysis graph showing the size distribution of synthetic NS—ZnO.

ZnO nanoparticles were induced so as to form a spindle structure. FIG. 2A is an SEM image of NS—ZnO (approximately 200 nm) synthesized with a uniform nanospindle structure. From the SEM image, it could be confirmed that a uniform NS—ZnO crystal having a spindle structure having a structure of sharp ends and a convex center was formed. FIG. 2B illustrates the size distribution data of the NS—ZnO nanomaterial, and it can be seen that the size of the prepared NS—ZnO is mainly distributed in a range of 180 to 200 nm.

Figure 3A:
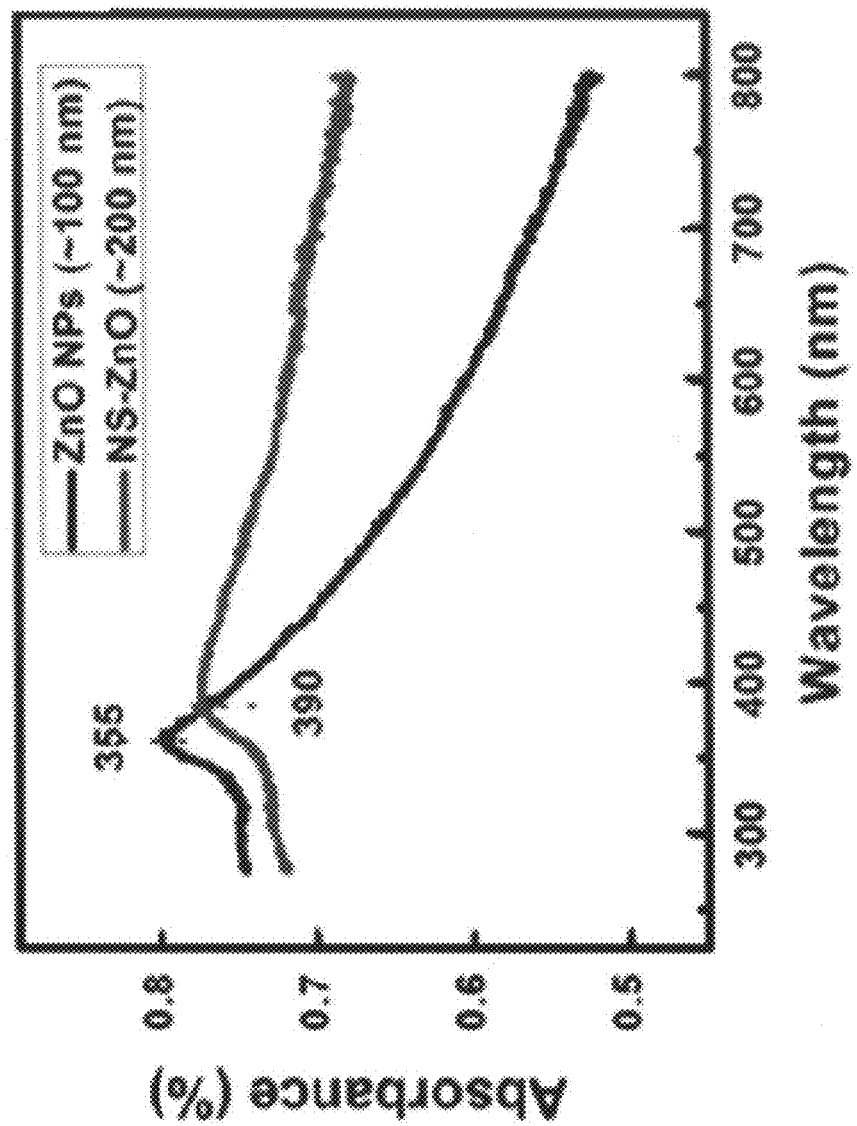
FIG. 3A illustrates the UV-visible light absorption spectra of ZnO nanomaterials (ZnO NP and NS—ZnO).
Figure 3B:
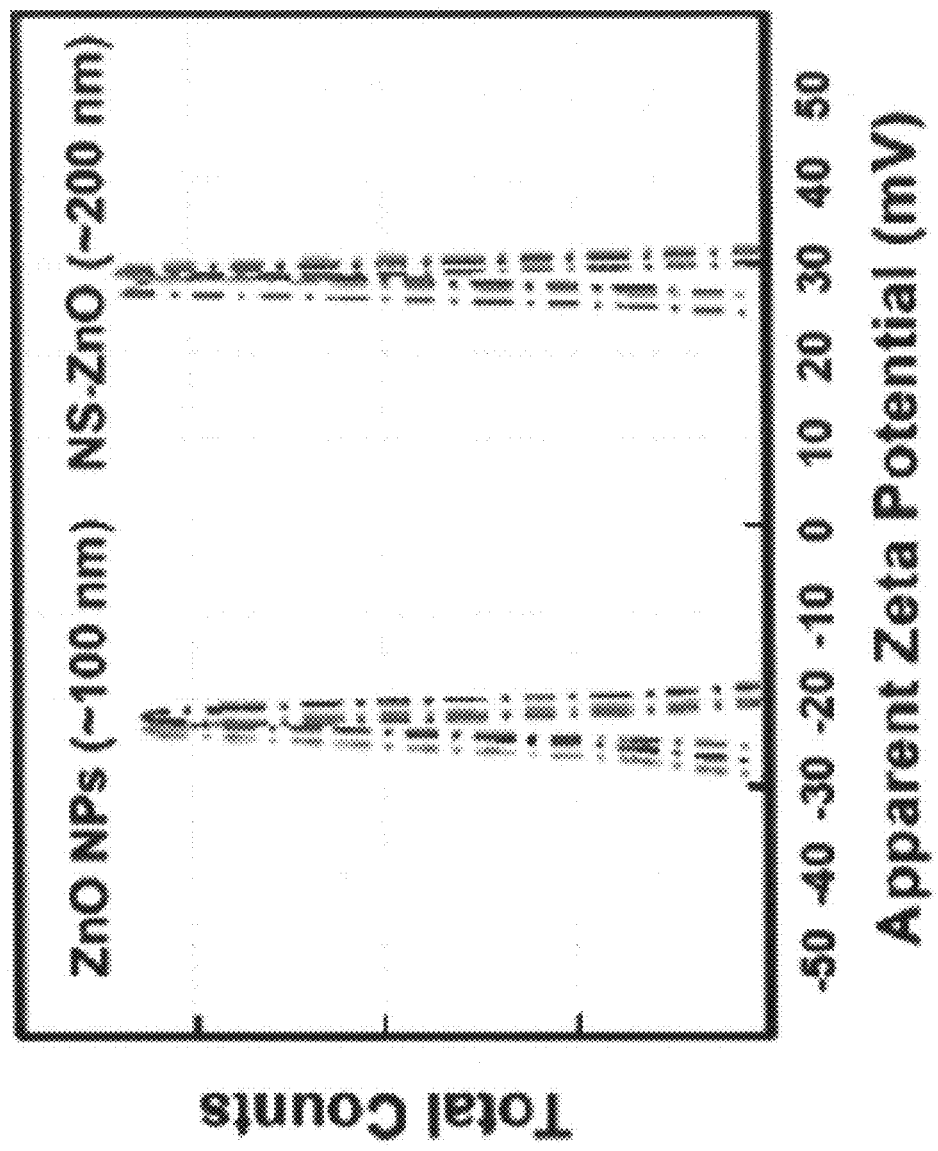
FIG. 3B is a view illustrating the zeta potentials of ZnO NP (approximately 100 nm) and NS—ZnO (approximately 200 nm).

In addition, the characteristics and morphological characteristics of metal elements were shown through ultraviolet visible light spectroscopy analysis as illustrated in FIGS. 3A to 3D. It was confirmed that the ZnO NSs (about 200 nm) having the spindle structure synthesized by the present inventors showed a characteristic peak at 390 nm (see FIG. 3A) compared to the commercially available ZnO NP (about 100 nm), the growth of ZnO NS was pure ZnO, and the width (red line) of the peak was also ZnO NS in the spindle form. The surface charge of the pure ZnO nanomaterial was measured by the zeta potential, and is shown in FIG. 3B. A special positive surface charge on ZnO—NS (about 200 nm) indicates that ZnO NS is covered by the $NH_4^+$ group derived from the improved $NH_4OH$ synthesis process of the present invention, and induces mild solubility. Furthermore, the positive surface charge may provide optimal conditions for additional biocompatibility applications.

(2) Homobifunctional Imidoester (HI) Modification

Next, according to FIG. 1, homobifunctional imidoester (HI) modification was performed. Two HI types of dimethyl pimelimidate dihydrochloride (DMP, Sigma, D8388-5G) or dimethyl suberimidate dihydrochloride (DMS, Sigma, 179523-5G) were used. Briefly, 4 mg of ZnO NS (40 mg/mL, 100 μL) and 4 mg of HI (DMP or DMS, 10 mg/mL, 400 μL) were dissolved in a solution amounting to 500 μL in a 1.5 mL-EP tube. The mixture was vibrated through an oscillating machine (Magic-mixer TMM-5). After 12 hours, the mixture was centrifuged at 12000 rpm for 5 minutes (Mini-Centrifuge, Labogene). The supernatant was removed, and the precipitate was washed twice with Milli-Q water. Finally, the precipitate was resuspended using 400 μL of Milli-Q water in order to obtain 10 mg/mL ZnO NS—HI. Thereafter, the precipitate was dried at 56° C. in a drying oven (Yamato, DX312C) overnight.

Figure 3C:
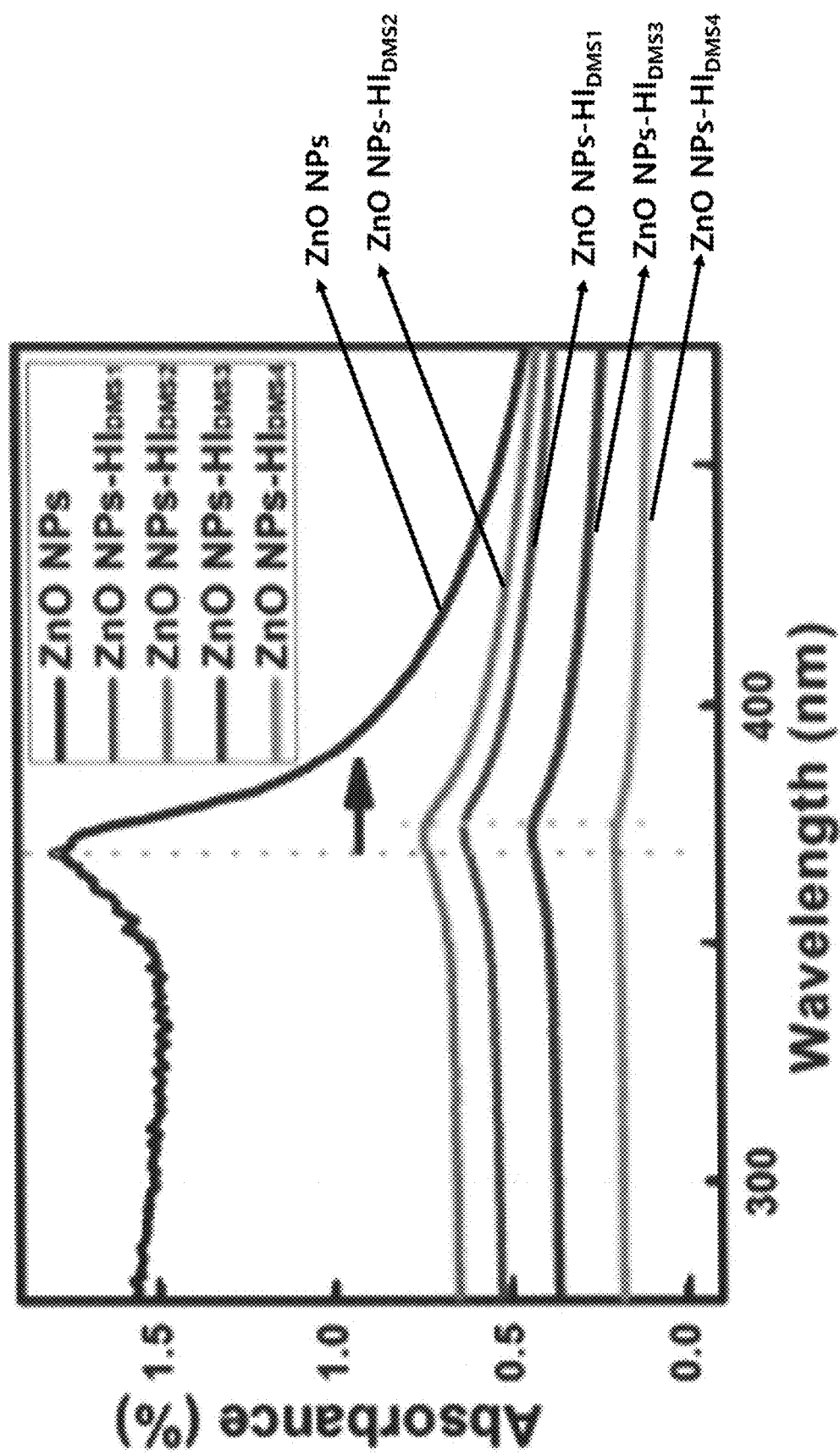
FIG. 3C illustrates the UV-visible light absorption spectra (red shift) of the materials after the modification of ZnO NP and HI.
Figure 3D:
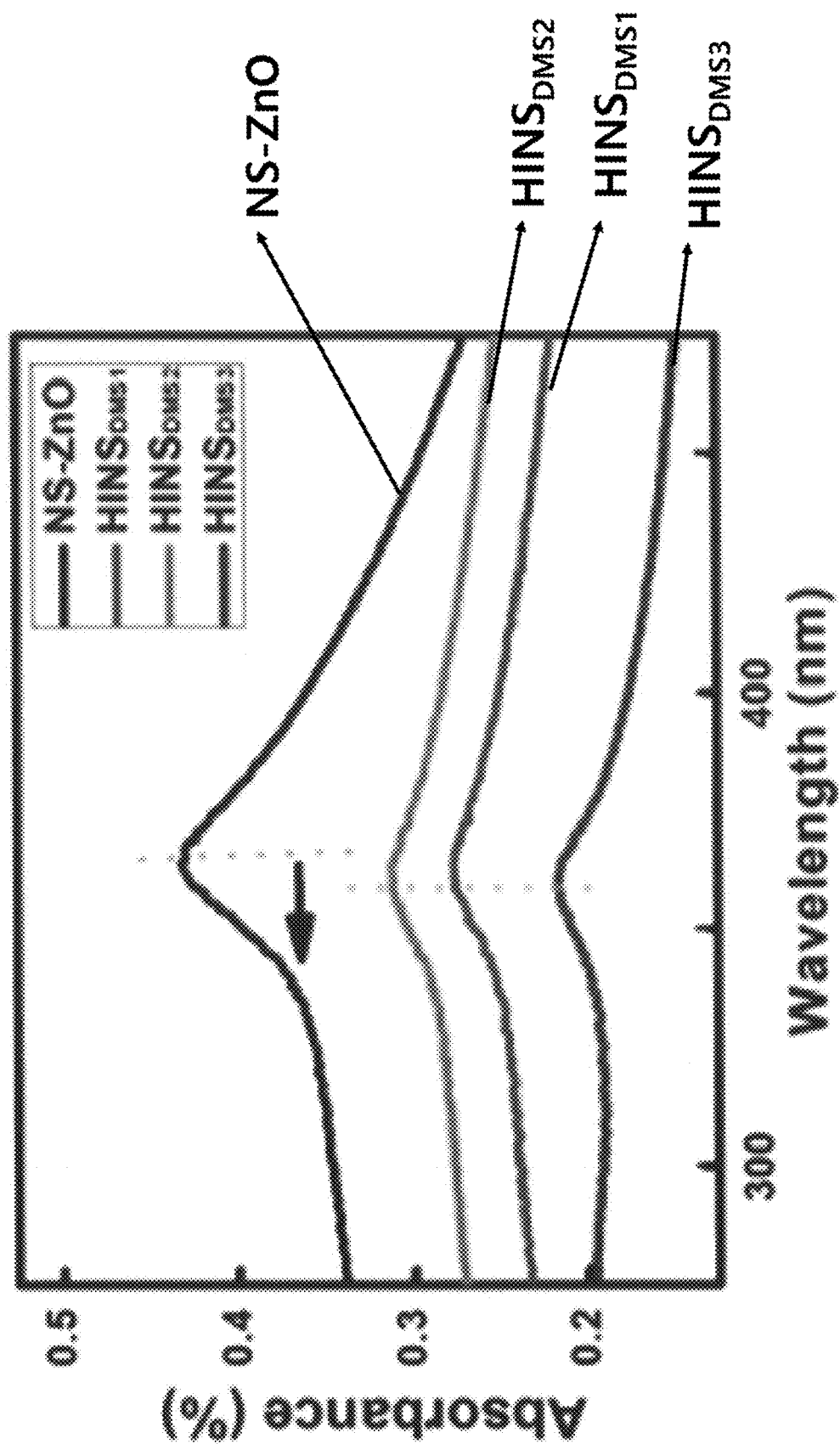
FIG. 3D illustrates the UV-visible light absorption spectra (blue shift) of the materials (HINS composites) after the modification of NS—ZnO and HI.

As illustrated in FIGS. 3C and 3D, the UV-visible light absorption spectra for HI-modified ZnO nanomaterials show ZnO NS—HI DMP and ZnO NS—HI DMS. FIG. 3C illustrates a red shift in HI-modified ZnO NP, which may be caused by energy loss due to HI (DMS) modification, and a wider peak range refers to a change in particle morphology due to fusion or aggregation. FIG. 3D illustrates a blue shift of the HINS composites, which have no clear morphological fusion or aggregation.

Figure 4:
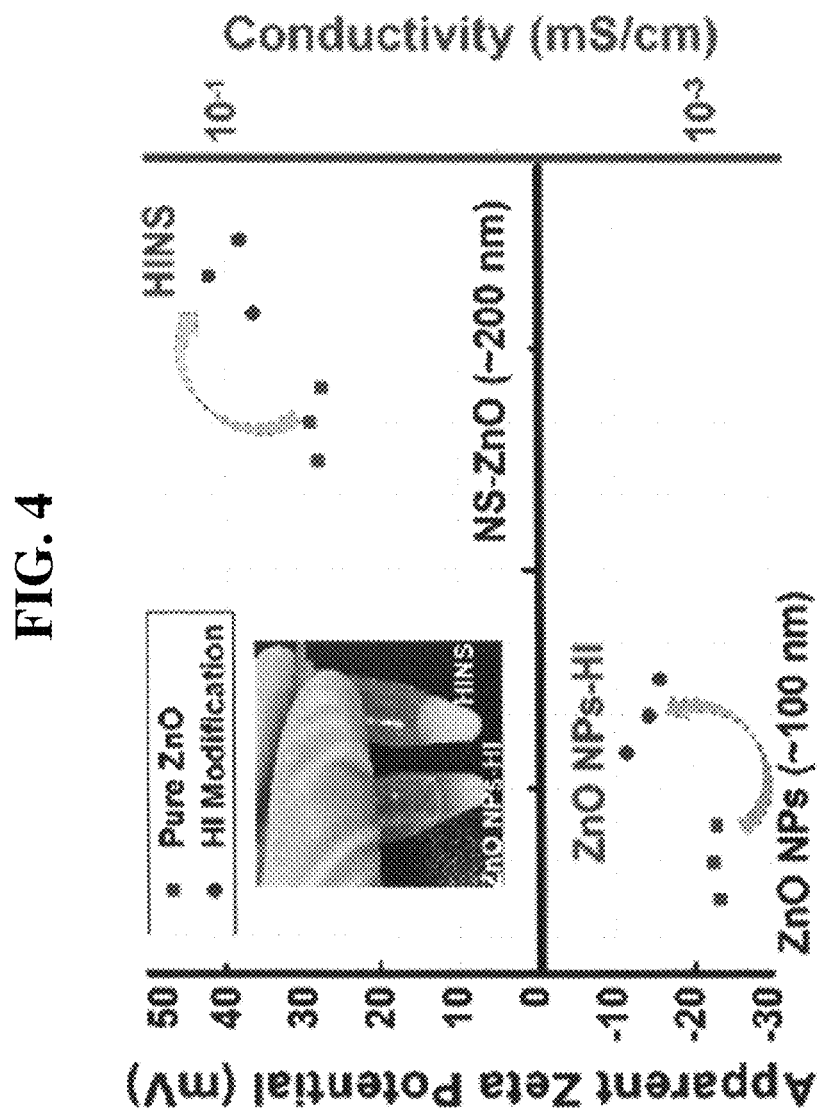
FIG. 4 shows the zeta potential of an HI-modified ZnO nanomaterial along with a photograph showing the state of soluble ZnO NP—HI and the HINS composite after being allowed to stand for 30 minutes.

FIG. 4 shows the zeta potential of an HI-modified ZnO nanomaterial along with a photograph showing the state of soluble ZnO NP—HI and the HINS composite after being allowed to stand for 30 minutes. The apparent surface zeta potential value indicates the surface activity of the material. After HI modification, the apparent zeta potential increased to +40 in ZnO NS, indicating active solution conduction. In contrast, ZnO NP showed opposite conditions in HI modification. ZnO NP—HI (DMP) is more easily aggregated. Here, when the HI (DMP)-modified ZnO nanomaterial was maintained at the same concentration (1 mg/mL) for 5 minutes, ZnO NP—HI (DMP) was more easily aggregated and precipitated, but ZnO NS—HI (DMP) showed better solubility. Meanwhile, the conductivity of ZnO NS—HI increased 102-fold compared to ZnO NP—HI (tested with Zetasizer Nano Series, Malvern).

Figure 5A:
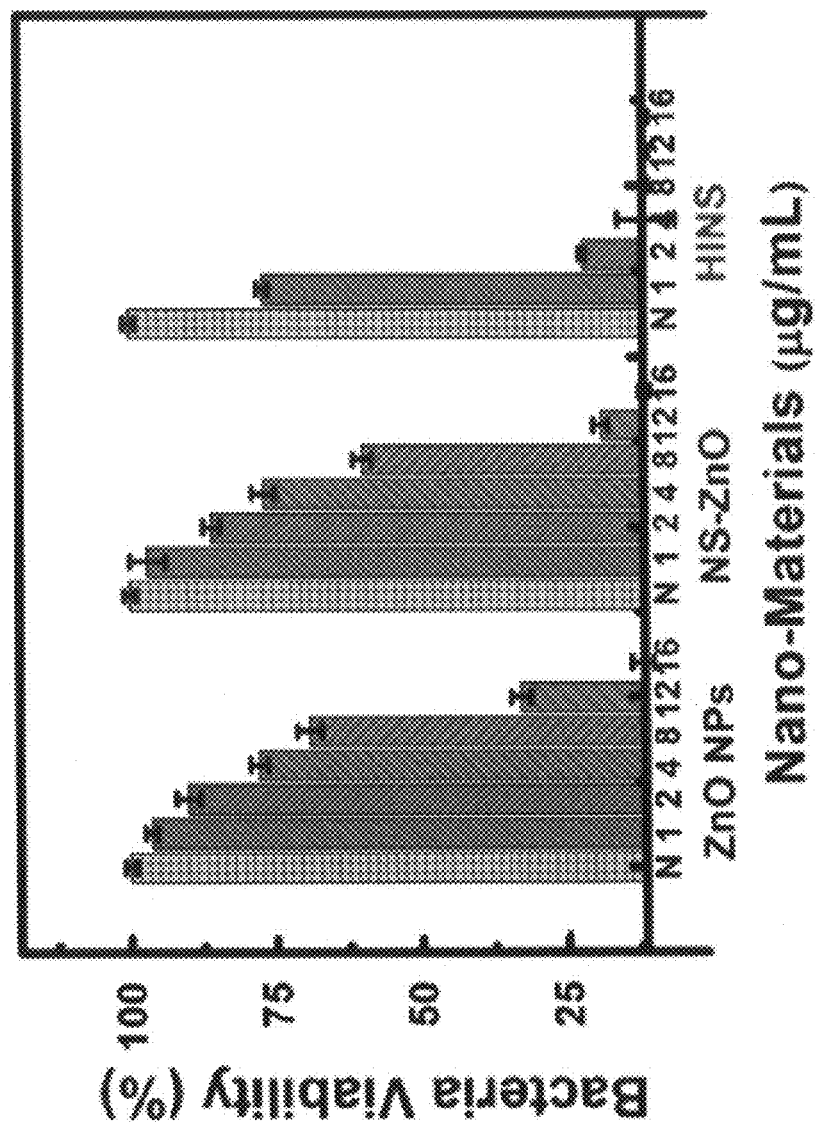
FIG. 5A shows the results of testing the antibacterial activity of ZnO nanomaterials against *E. coli* at various concentrations (1 to 16 µg/mL) (12-hour culture).
Figure 5B:
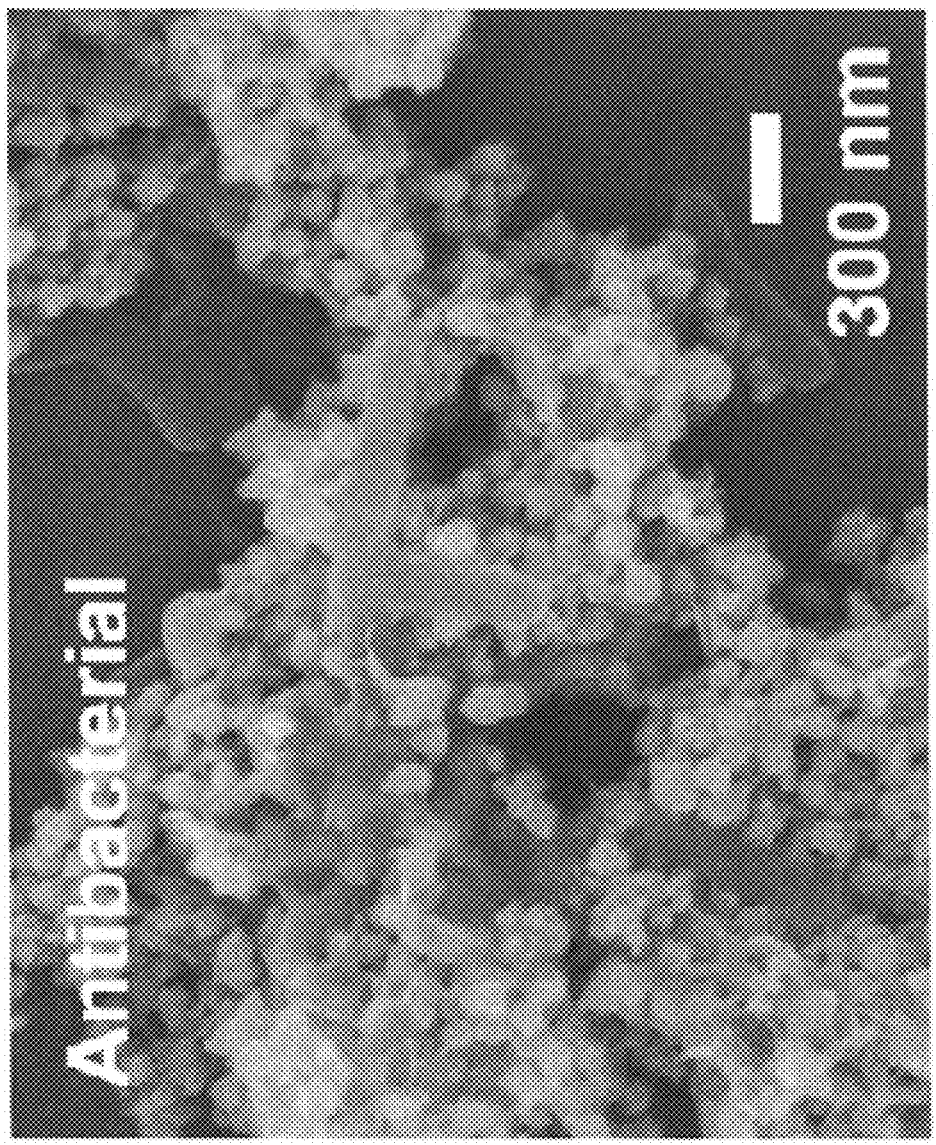
FIG. 5B is an SEM image showing that NS—ZnO (approximately 200 nm) lyses *E. coli;*

[Test Example 1] Evaluation of Antibiotic Activity (1) Evaluation of Antibacterial Activity Antibacterial activity was tested using Gram-negative bacteria (*Escherichia coli* and *Salmonella*), and 10 μg/mL test nanomaterials were put into tubes including a bacterial suspension. After reaction at 37° C. to 210 rpm overnight, the absorbance of each sample was measured at an OD of 600 nm. Bacterial viability was confirmed for ZnO nanomaterials at continuous concentrations of 1 μg/mL to 16 μg/mL. From FIG. 5A, it can be seen that HINS (ZnO NS—HI (DMP)) completely inhibited bacterial growth even at very low concentrations (4 μg/mL), showing better antibacterial characteristics than other ZnO nanomaterials, that is, ZnO NP and ZnO NS. In addition, the antibacterial activity of NS—ZnO is even better than that of ZnO NP at the same concentration, which seems to be due to its active surface characteristics (positive surface charge easily attracts bacteria) and physical morphology (the sharp protrusions of NS—ZnO). Meanwhile, the SEM image illustrated in FIG. 5B shows that ZnO NS is adsorbed on a pathogen (*E. coli*) and the membrane of the pathogen is lysed.

(2) Evaluation of Antifungal Activity

Figure 6A:
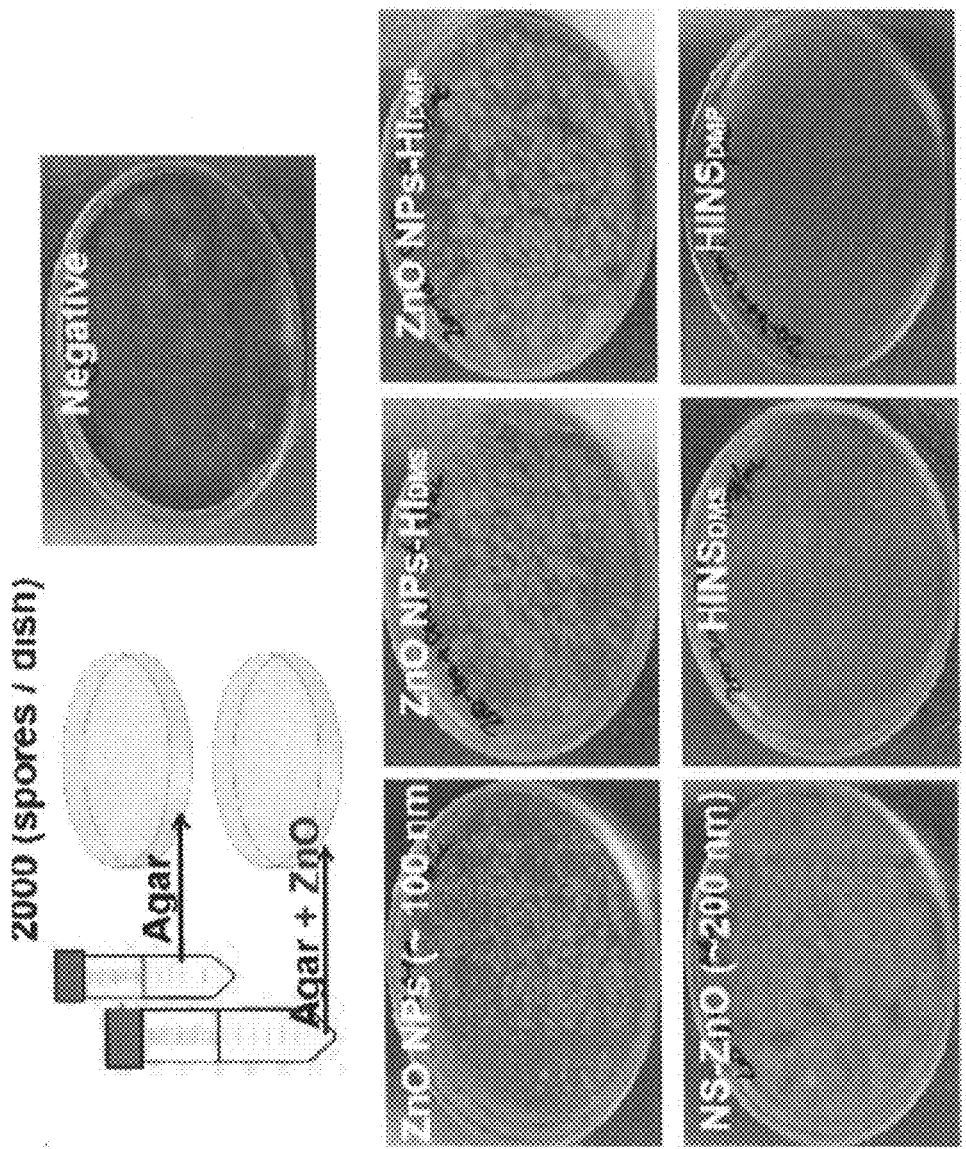
FIGS. 6A and 6B illustrate the results of testing the antifungal activity of ZnO nanomaterials (2000 *Aspergillus* spores/dish, cultured at 25° C., 7 days after culture). Specifically.
Figure 6B:
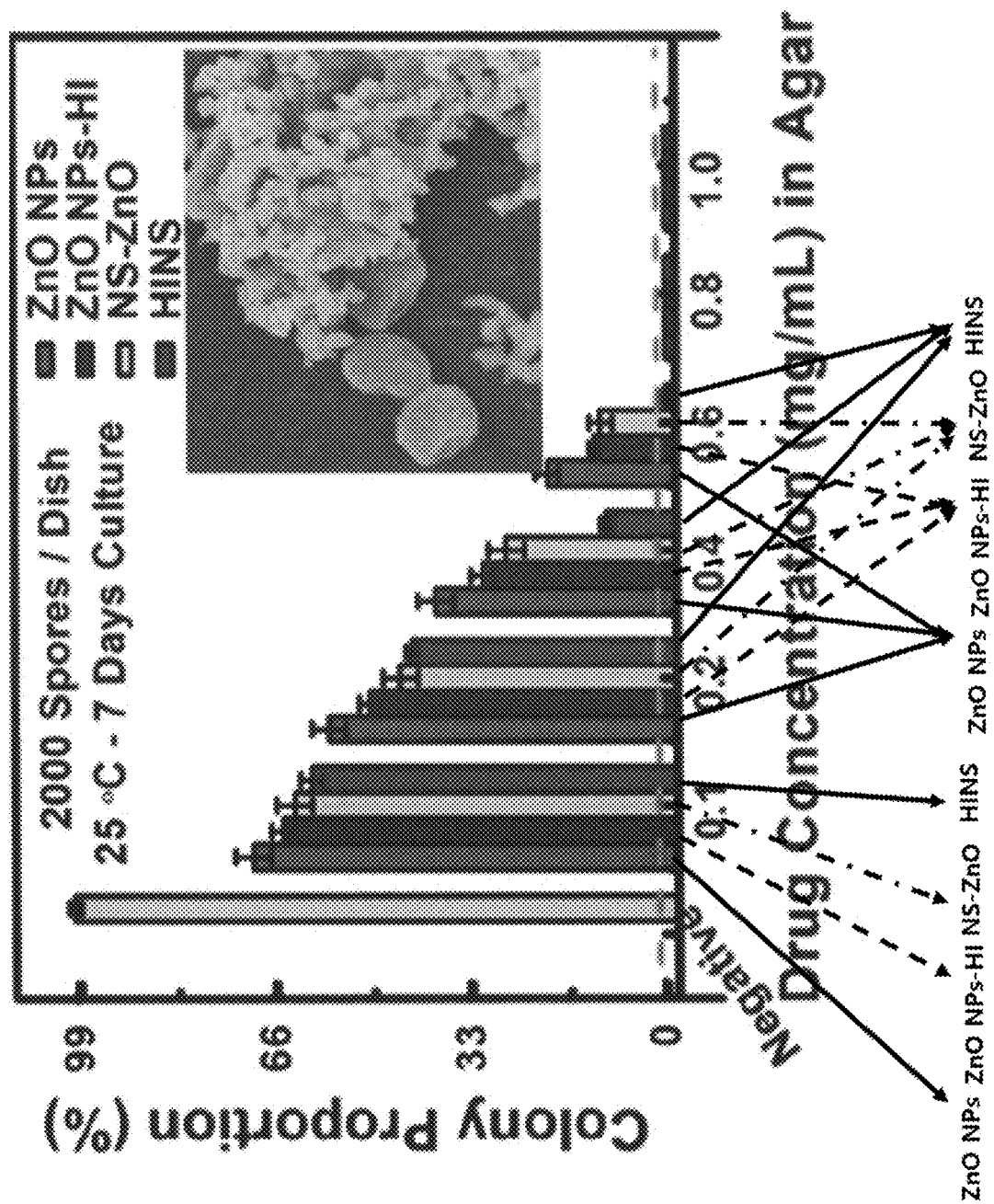

*Aspergillus fumigatus* was used to evaluate antifungal activity. In the SEM image, the present inventors confirmed that spores covered the ZnO nanomaterials, and the membrane was weakened and destroyed (FIG. 6B).

Two methods were used, and first, the ZnO nanomaterials at a concentration of 0.1, 0.2, 0.4, 0.6, 0.8 and 1.0 mg/mL in sterile agar plates were mixed with mold and cultured (2000 spores, 25° C., 7 days). To perform antifungal analysis, a dextrose agar medium was prepared. A specific solid medium including various doses of test nanomaterials (ZnO nanomaterials) was prepared. Growth photographs were recorded every 12 hours, mold growth areas were measured with Image-J, and the growth rate of each treatment group was analyzed compared to the control sample. The colony growth ratio in the continuous culture was confirmed. From FIG. 6B, it could be seen that the viability of fungal spores decreased as the drug concentration increased. The HINS composite at a concentration of 0.4 mg/mL showed significant inhibitory ability, which was much stronger than the higher concentrations of other nanomaterials (0.6 mg/mL). From FIG. 6A, it can be confirmed that the cultured agar is clean at 0.6 mg/mL HINS composite, showing that the HINS composite not only inhibits the growth of mold spores, but also kills them.

Figure 7A:
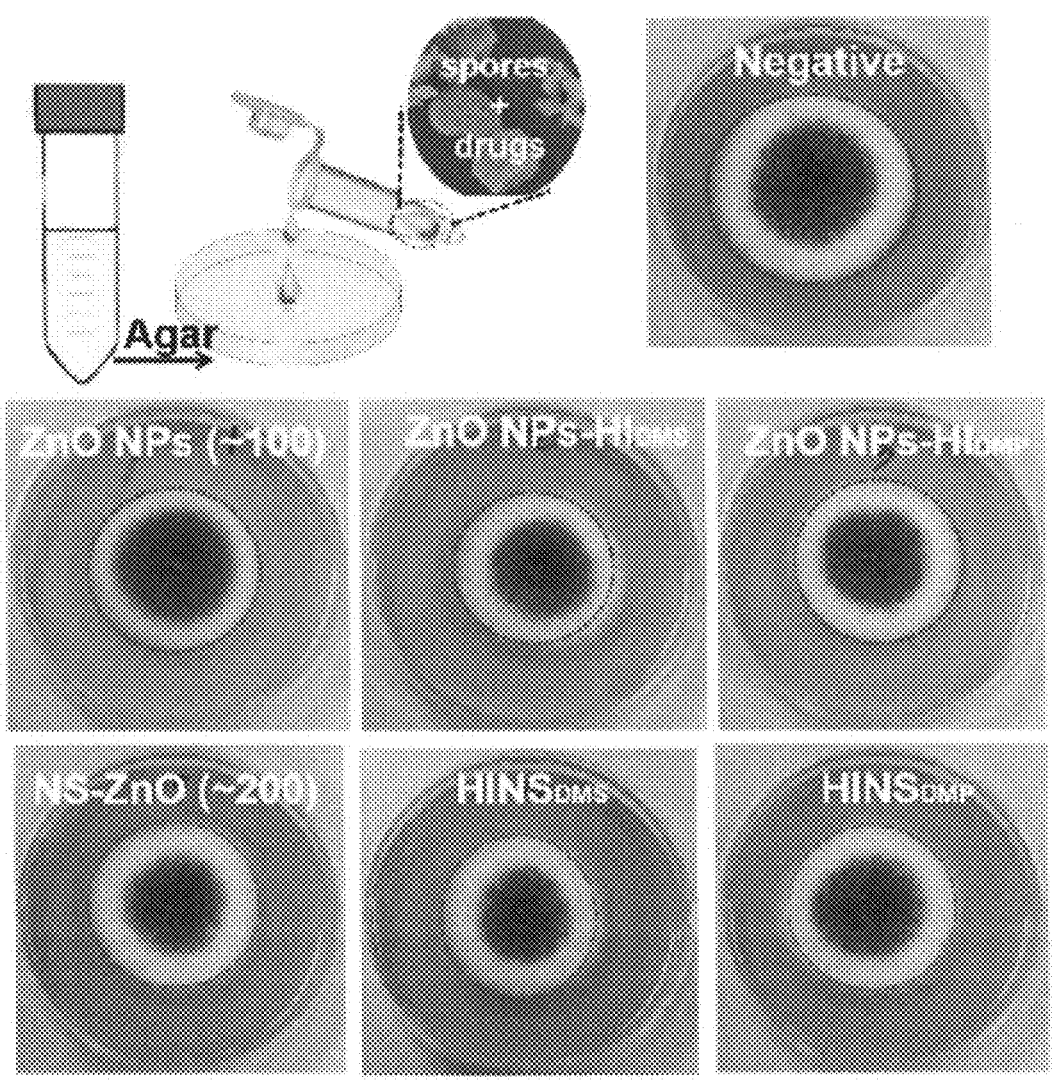
FIGS. 7A and 7B illustrate the results of testing the antifungal activity of ZnO nanomaterials (0.2 mg/mL, 50 µL) (400 *Aspergillus* spores/dish, cultured at 25° C., culture, 10-day culture conditions).
Figure 7B:
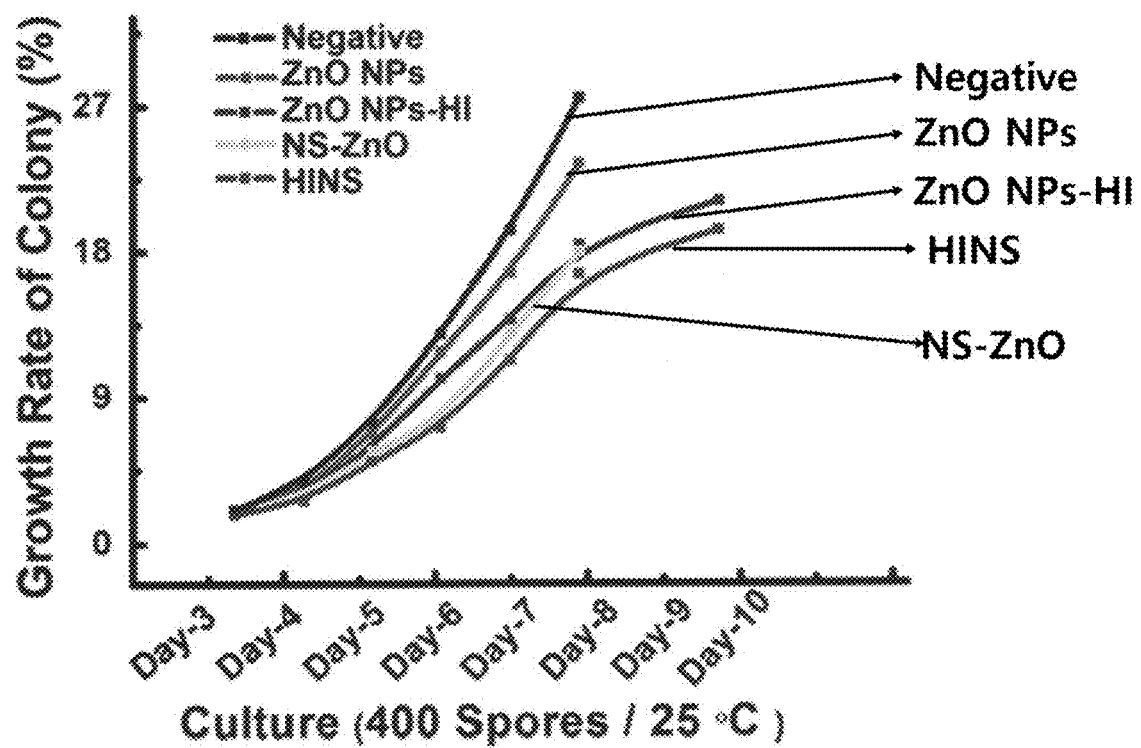

In FIGS. 7A and 7B, it was observed that the colonies spread after being transplanted into the center of the agar and, and the growth rate could be calculated by measuring the surface area of the colony. The surface area of each colony (400 spores/dish, 0.01 mg/mL drug concentration) was recorded daily and the growth rate is illustrated in FIG. 7B as a graph. The growth rate when the HI-modified nanomaterial (ZnO NP—HI and HINS composite) was used was significantly slower than other nanomaterials for the first 7 days, and then the growth rate of the HI-modified nanomaterial became almost constant for a period between day 7 and day 14. This confirms that the antifungal activity is maintained for a long period of time by the HI modification according to the present invention.

[Test Example 2] Evaluation of Effect According to Environment

Figure 8A:
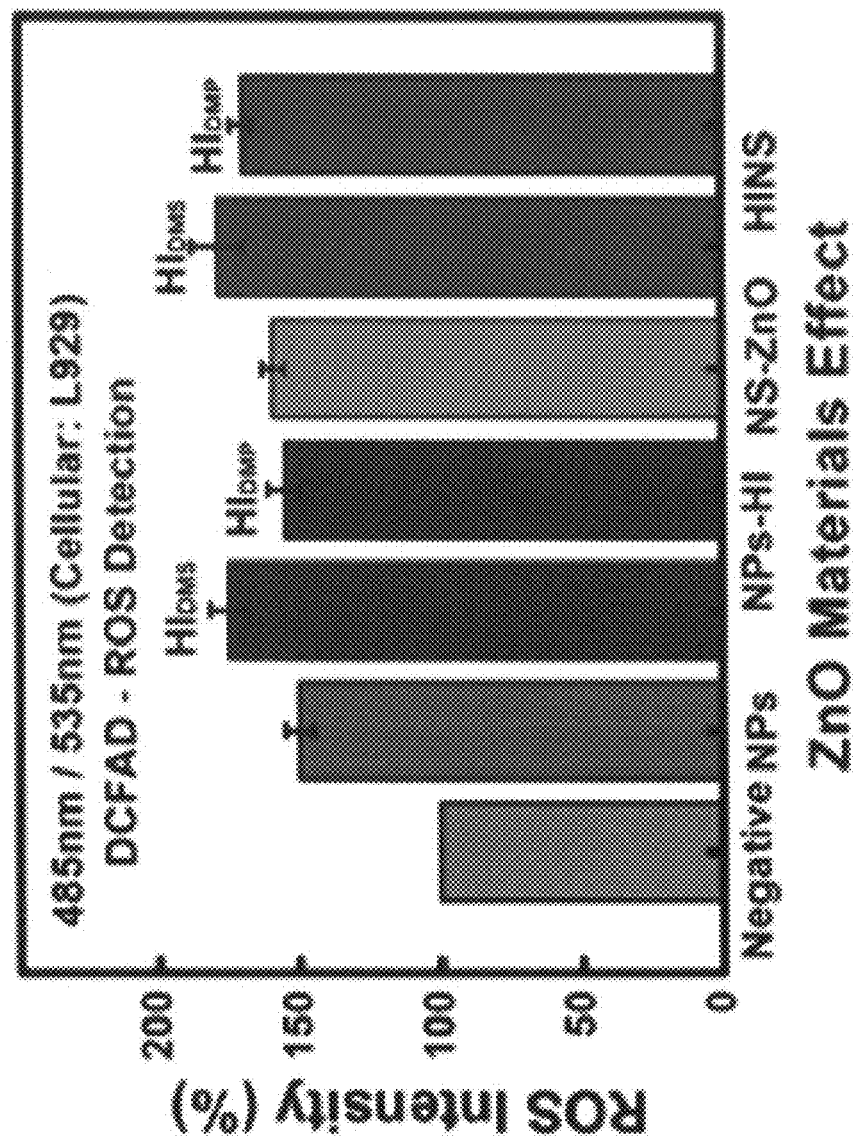
FIG. 8A is a graph showing the effect of ROS.

A DCFDA-ROS kit test was performed, and the results are illustrated in FIG. 8A. The results show that the ZnO nanomaterial used in the present experiment had a ROS intensity 1.5-fold higher than that in a general cell environment (provided that the ROS intensity is within a safe cell balance range of oxidative stress) and the oxidative stress of the L929 cell environment after HI (DMS and DMP) modification increased.

Figure 8B:
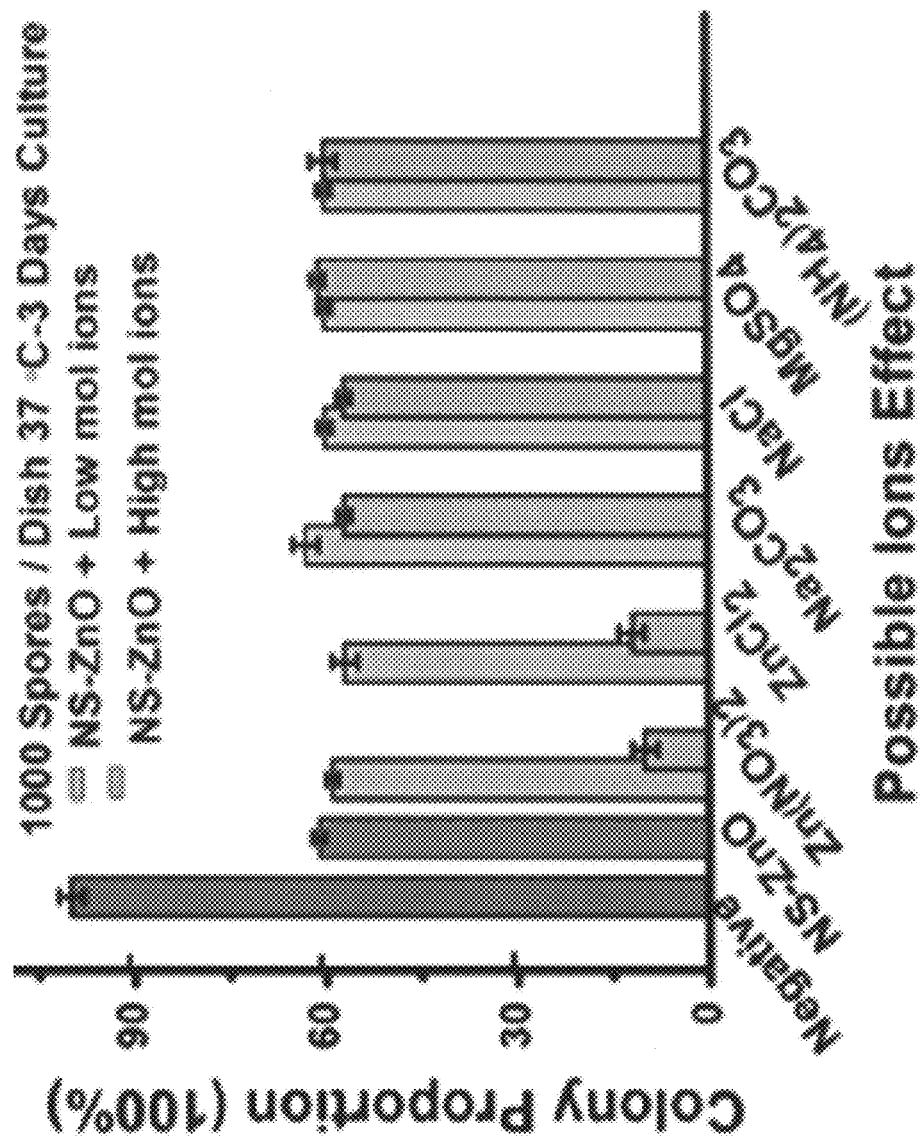
FIG. 8B is a graph showing the effect by peripheral ions.

To investigate the effect of ions on fungal growth, salt solutions were added at a high molecular concentration (0.1 M, 10 µL) and a low molecular concentration (0.1 M, 10 µL) and fungi were cultured at 37° C. under conditions of 1000 Aspergillus spores/dish. The results are illustrated in FIG. 8B based on the colonies on day 3 of culture. It can be seen that the $Zn^{2+}$ ions supplied by $Zn(NO_3)_2$ and $ZnCl_2$ had a greater effect than the $Na^+$, $Mg^{2+}$ or $NH_4^+$ ions supplied by $Na_2CO_3$, NaCl, $MgSO_4$, and $(NH_4)_2CO_3$, and the effect of supplementation with high-concentration mol (10M) $Zn^{2+}$ was almost 2-fold that of pure NS—ZnO.

Figure 8C:
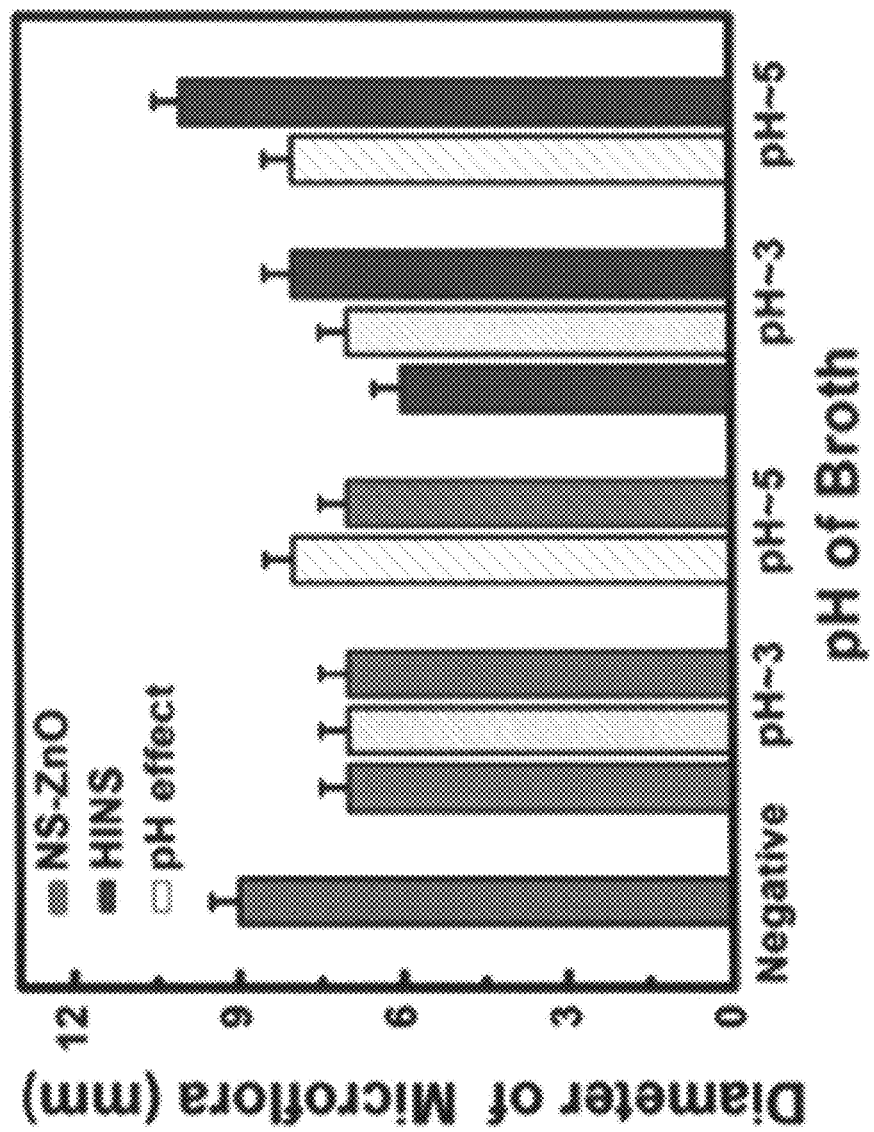
FIG. 8C is a graph showing the effect according to broth pH.
Figure 8D:
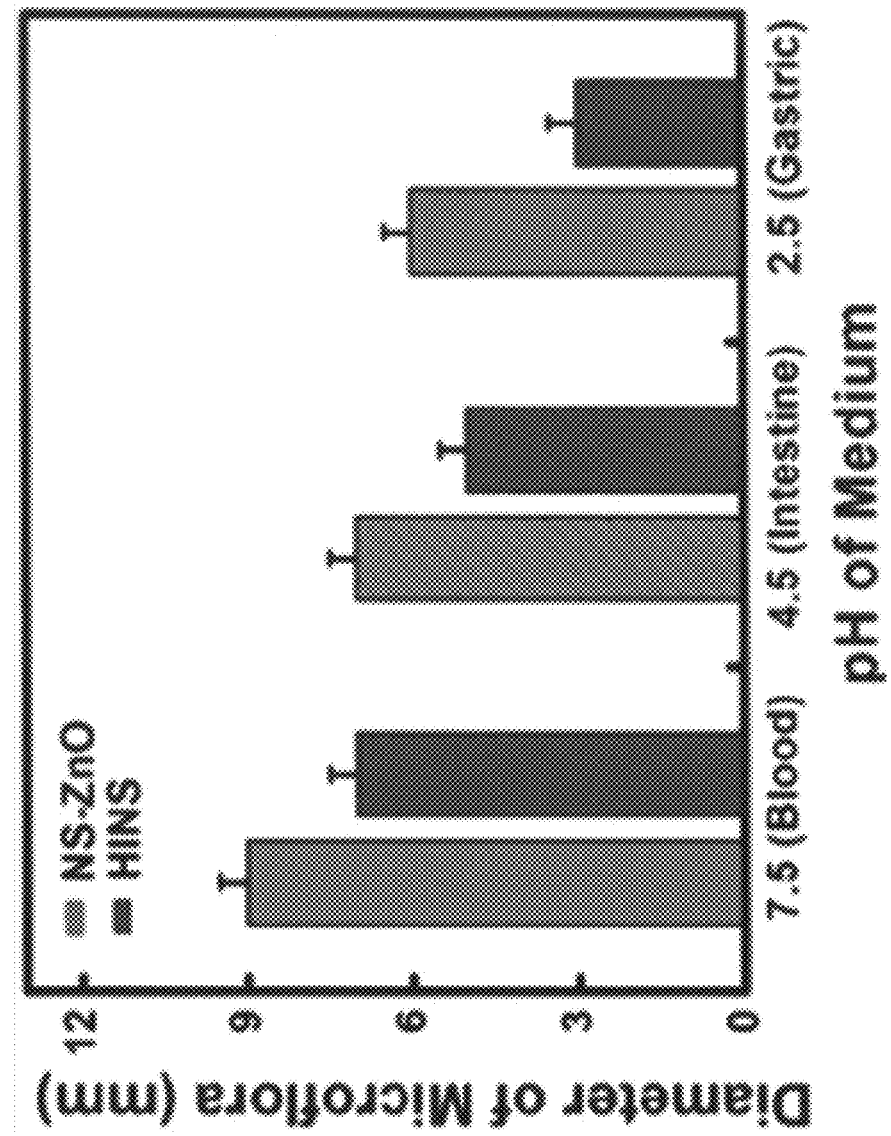
FIG. 8D is a graph showing the effect according to medium pH.

To investigate the effect of pH, the pH of a broth was adjusted, and the results are illustrated in FIG. 8C. It can be seen that as the pH is adjusted to acidic, the antifungal activity of the HINS composite disappeared. However, when the pH test was performed in an agar medium, both the NS—ZnO and HINS composites maintained antifungal properties, which can be confirmed in FIG. 8D. PH 7.5 (blood), pH 4.5 (intestines), and pH 2.5 (stomach) were set as pH values similar to those in the human body. From FIG. 8D, the excellent antifungal activity of the HINS composite can be confirmed at each pH, suggesting that the HINS composite can be used as an ointment on the wound surface. Furthermore, the maintenance of activity in the blood pH medium suggests that the HINS composite can be safely administered intravenously.

[Test Example 3] Combination Experiment with Other Antibiotics

Figure 9A:
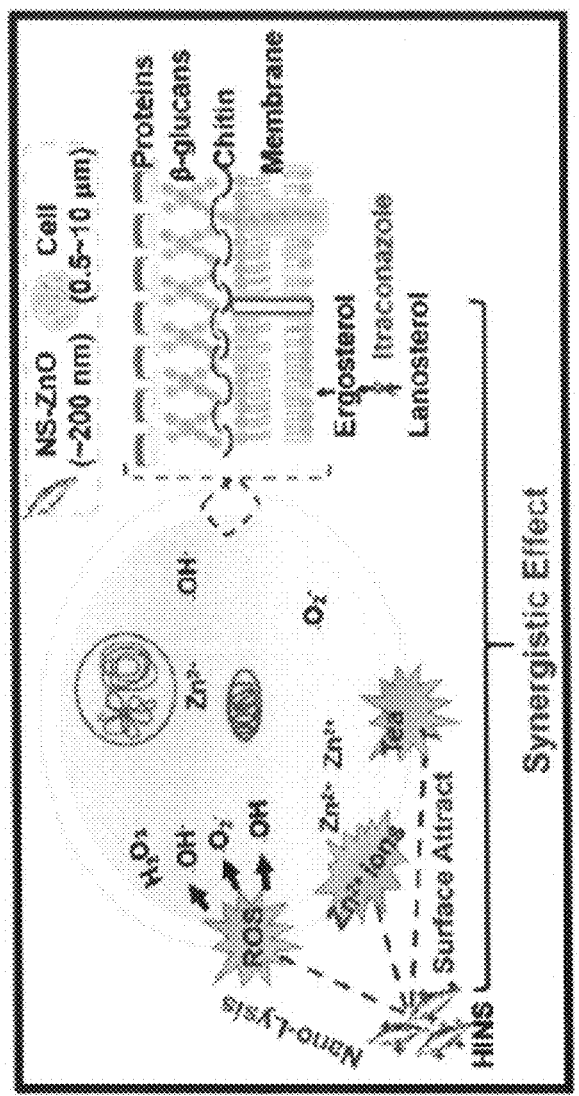
FIG. 9A is a view illustrating an antifungal mechanism hypothesis for synergistic effects when the HINS composite is used in combination with other antibiotic materials.

FIG. 9A shows a mechanism hypothesis explaining the synergistic effect of the combined use of the composite of the present invention with existing antibiotics, and the improved antifungal characteristics of the HINS composite appear to be due to an imidoester functional group helping to extend the lifetime of ROS and $Zn^{2+}$ and damage the spore wall/membrane.

Figure 9B:
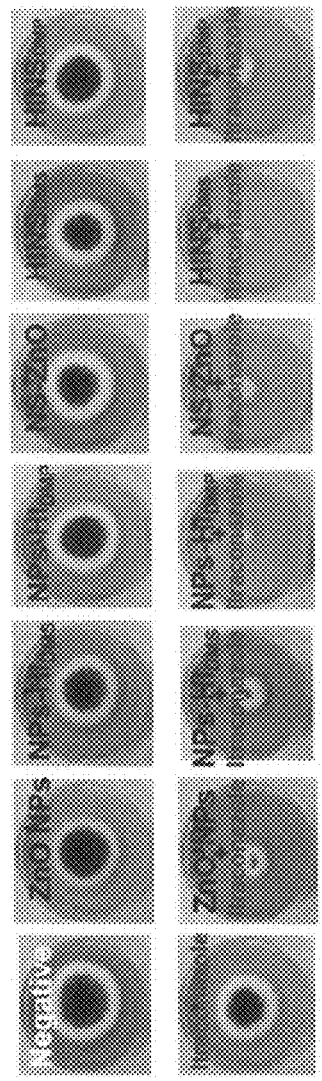
FIG. 9B illustrates the effects by the combination with other antibiotic materials through *Aspergillus* colony photographs.
Figure 9C:
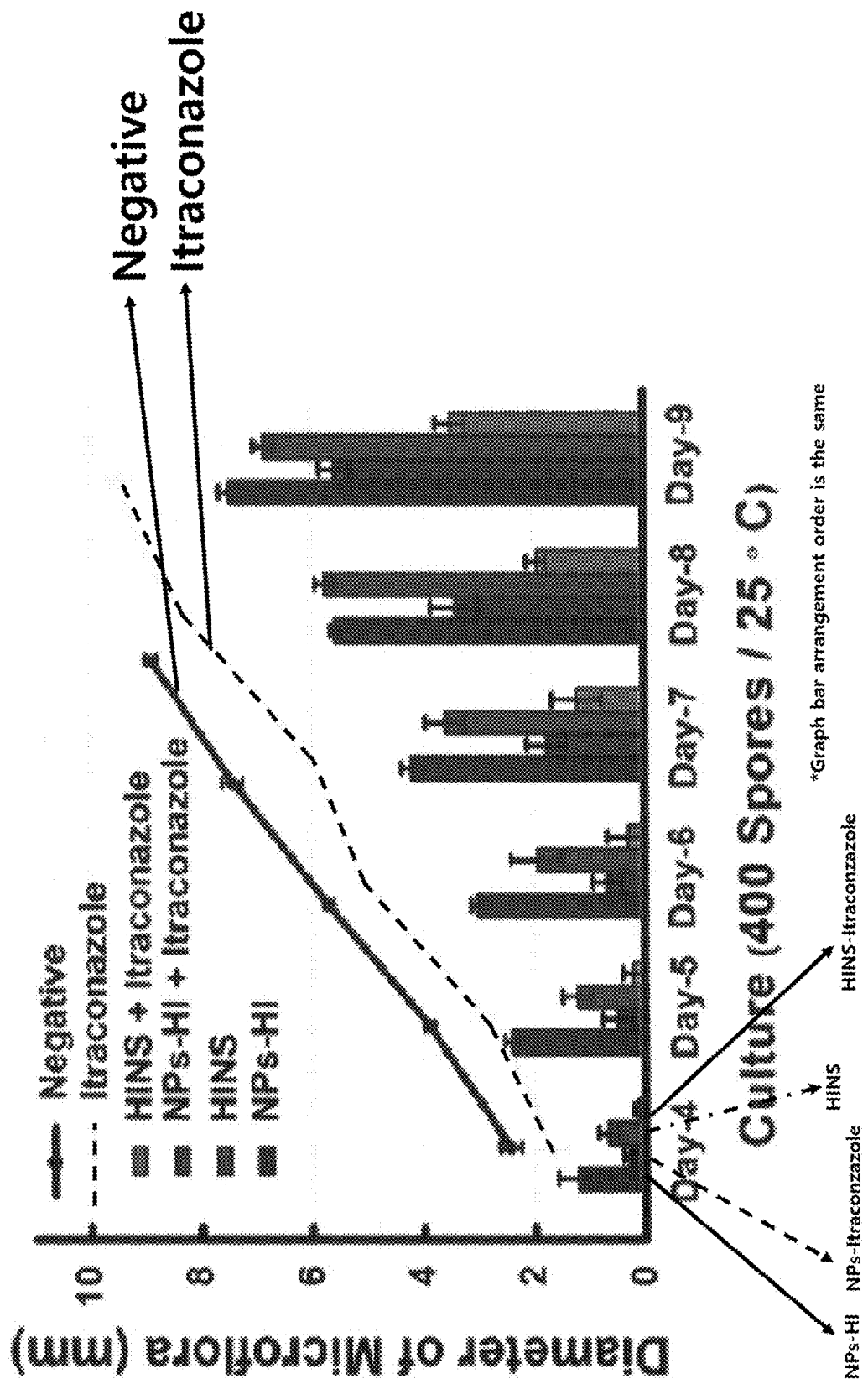
FIG. 9C illustrates the results of recording the diameters of *Aspergillus* colonies at 25° C. daily for 9 days (400 spores/dish, 50 μL of 0.1 mg/mL ZnO nanomaterials, 6 μg/mL itraconazole)

NS—ZnO and itraconazole were used to confirm the synergistic effect according to the above-described combined use, and here, the concentration of itraconazole was set to 6 µg/mL and the concentration of ZnO nanomaterials was set to 0.1 mg/mL. The diameter of the Aspergillus colony was recorded daily, and the results are illustrated in FIGS. 9B and 9C. FIG. 9B shows the Aspergillus colony on day 6 of culture. According to the results, it was found that not only antifungal activity was improved by the combined use, but also inhibitory ability was maintained until after day 9 of culture. On day 5, the HINS composite showed an inhibition rate of 70%, whereas the inhibition rate of ZnO NP—HI was 35%. The slower growth rate of Aspergillus colonies when the HINS composite is used compared to the control means that the HINS composite can be used for long-term administration and the dose frequency may be reduced. In particular, after day 6 of culture, the growth rate increased rapidly in an itraconazole alone administration group and a ZnO alone administration group, which means that the above drug cannot inhibit the growth of new spores. In contrast, in the case of the combination administration group of the HINS composite and itraconazole, the inhibitory effect was almost 90% even on day 6 of culture due to the synergistic effect.

[Test Example 4] In Vitro Blood Test

Figure 10A:
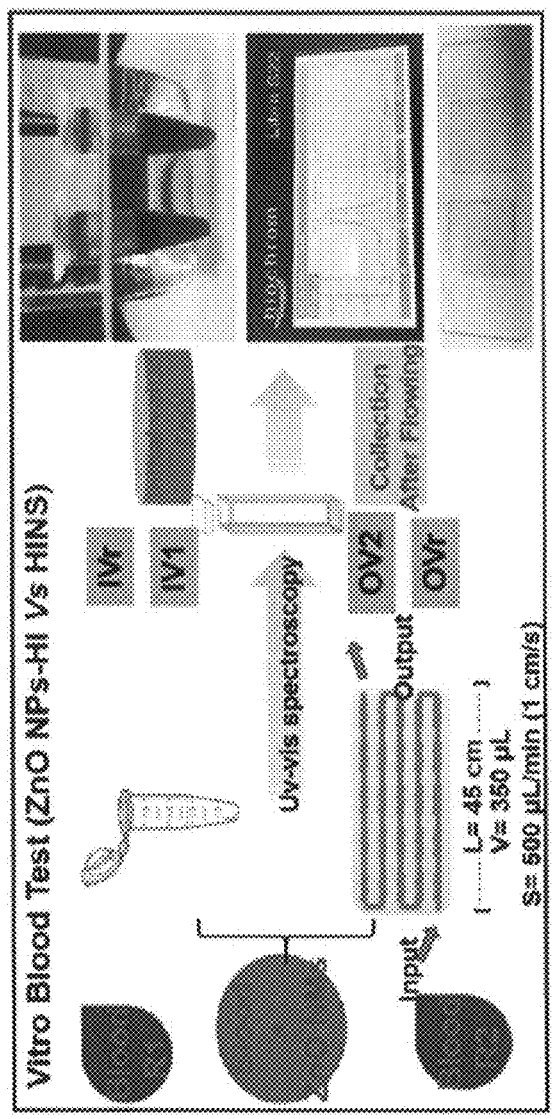
FIG. 10A is a view schematically illustrating an in vitro blood test method.
Figure 10B:
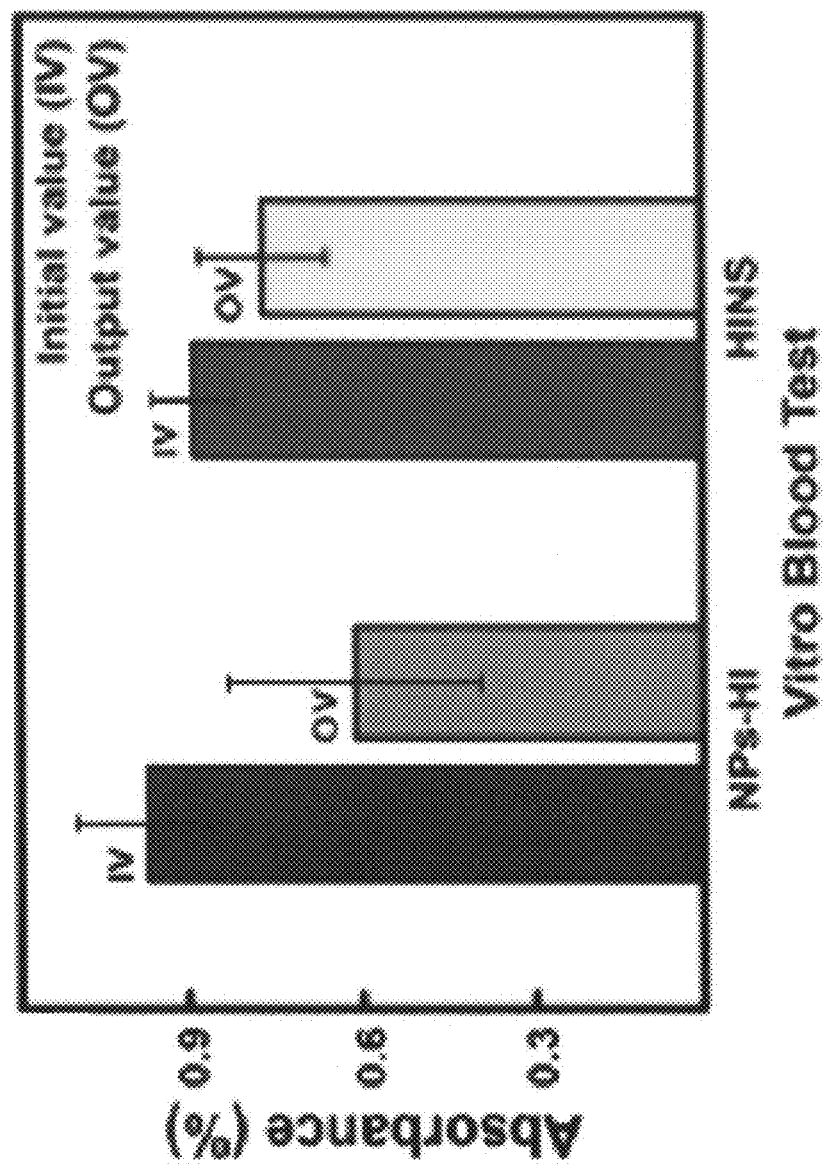
FIG. 10B is a graph showing the initial absorbance value (IV) of the ZnO nanomaterial and the absorbance value (OV) after the in vitro blood test.
Figure 10C:
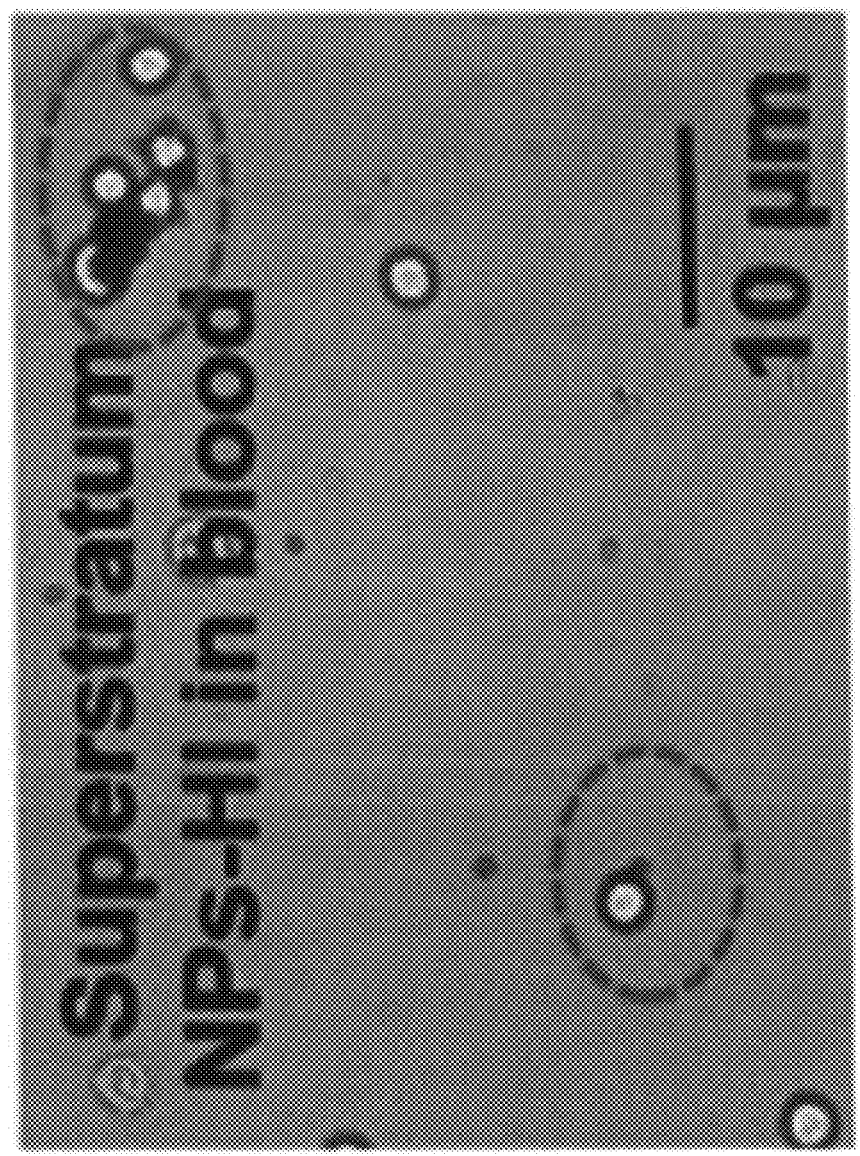
FIGS. 10C and 10D are micrographs illustrating the upper layers of the ZnO NP—HI and HINS composite systems in blood, respectively.
Figure 10D:
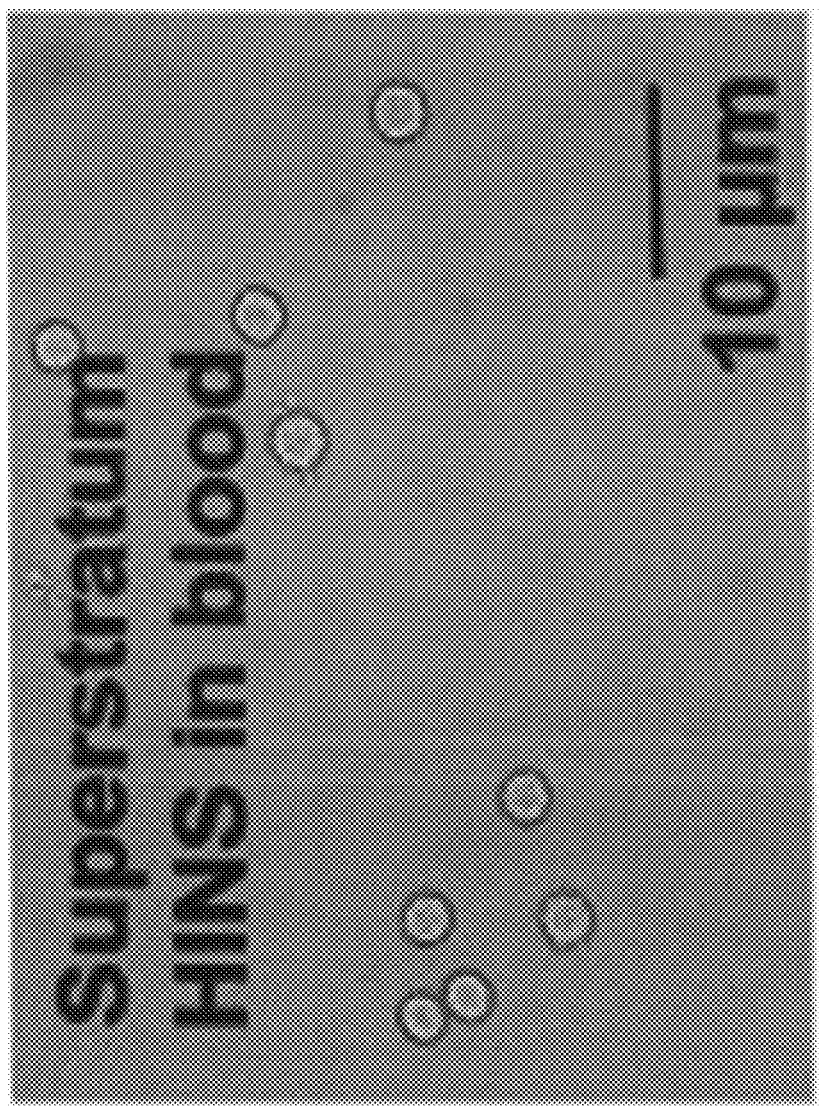
Figure 11A:
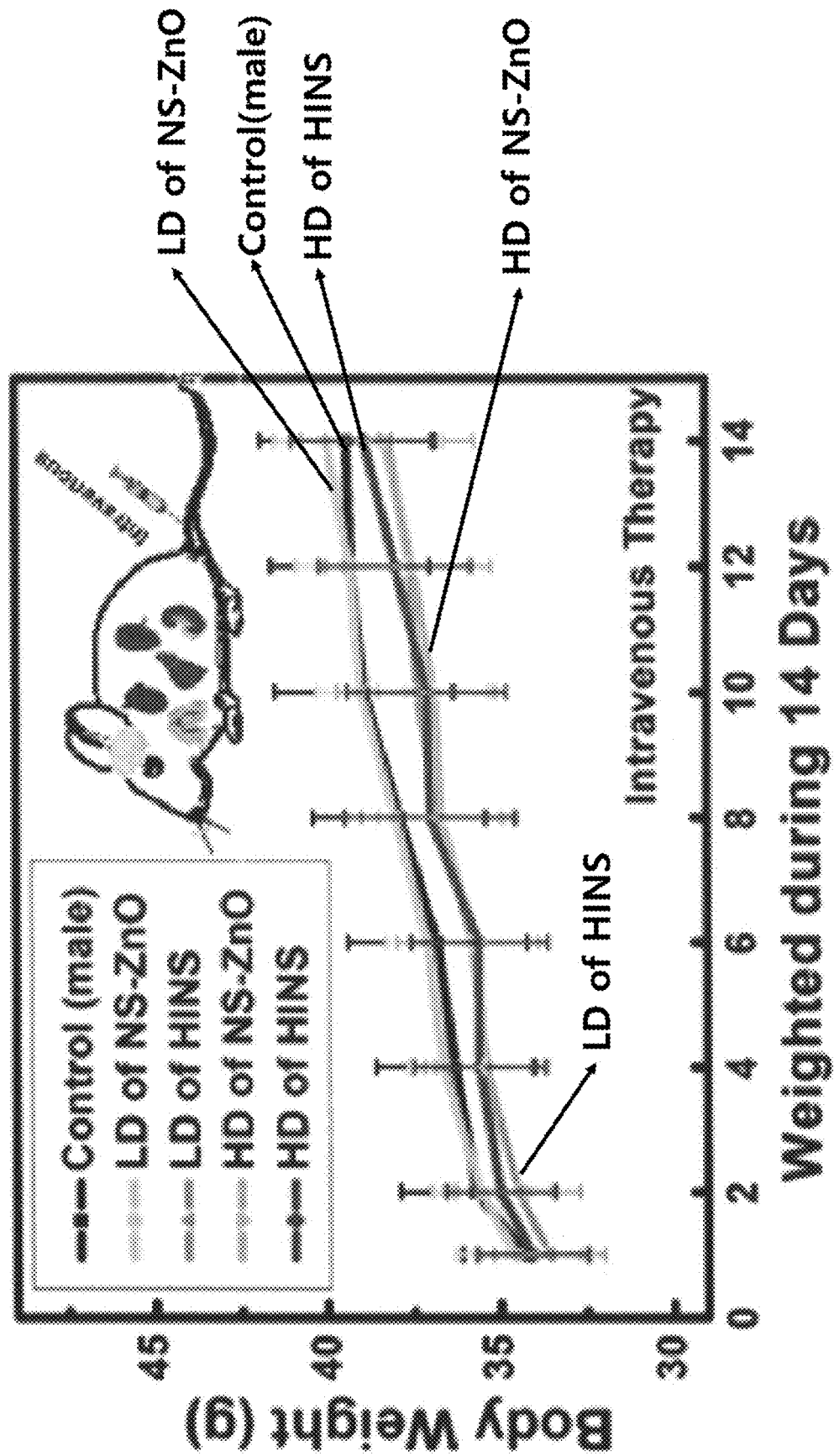
FIGS. 11A to 11F are the results of in vivo toxicity and biocompatibility tests using the HINS composite. The NS—ZnO or HINS composite was intravenously administered at a low dose (LD) and high dose (HD), and the body weights of the mice were monitored for 14 days.
Figure 11B:
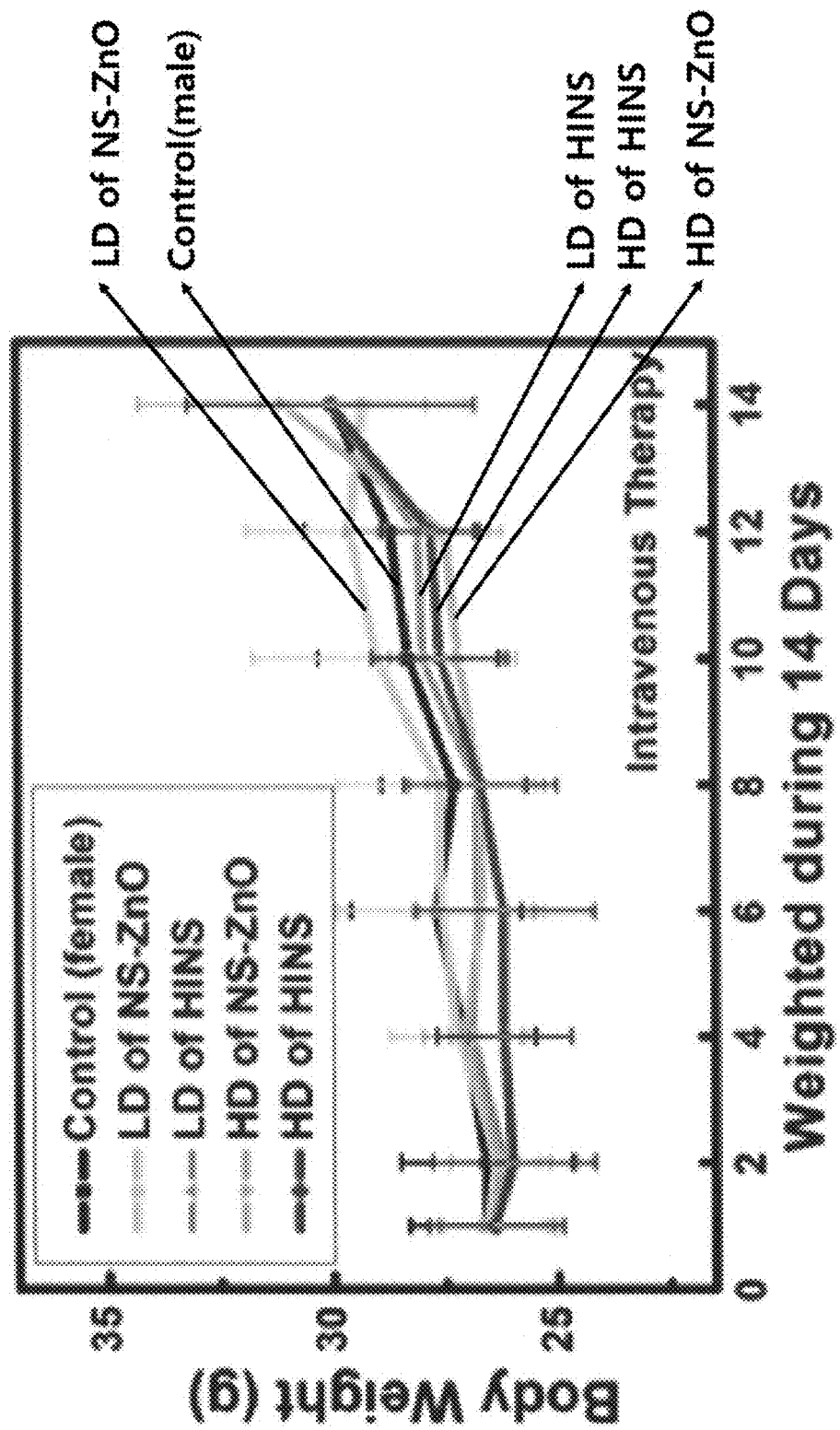
Figure 11C:
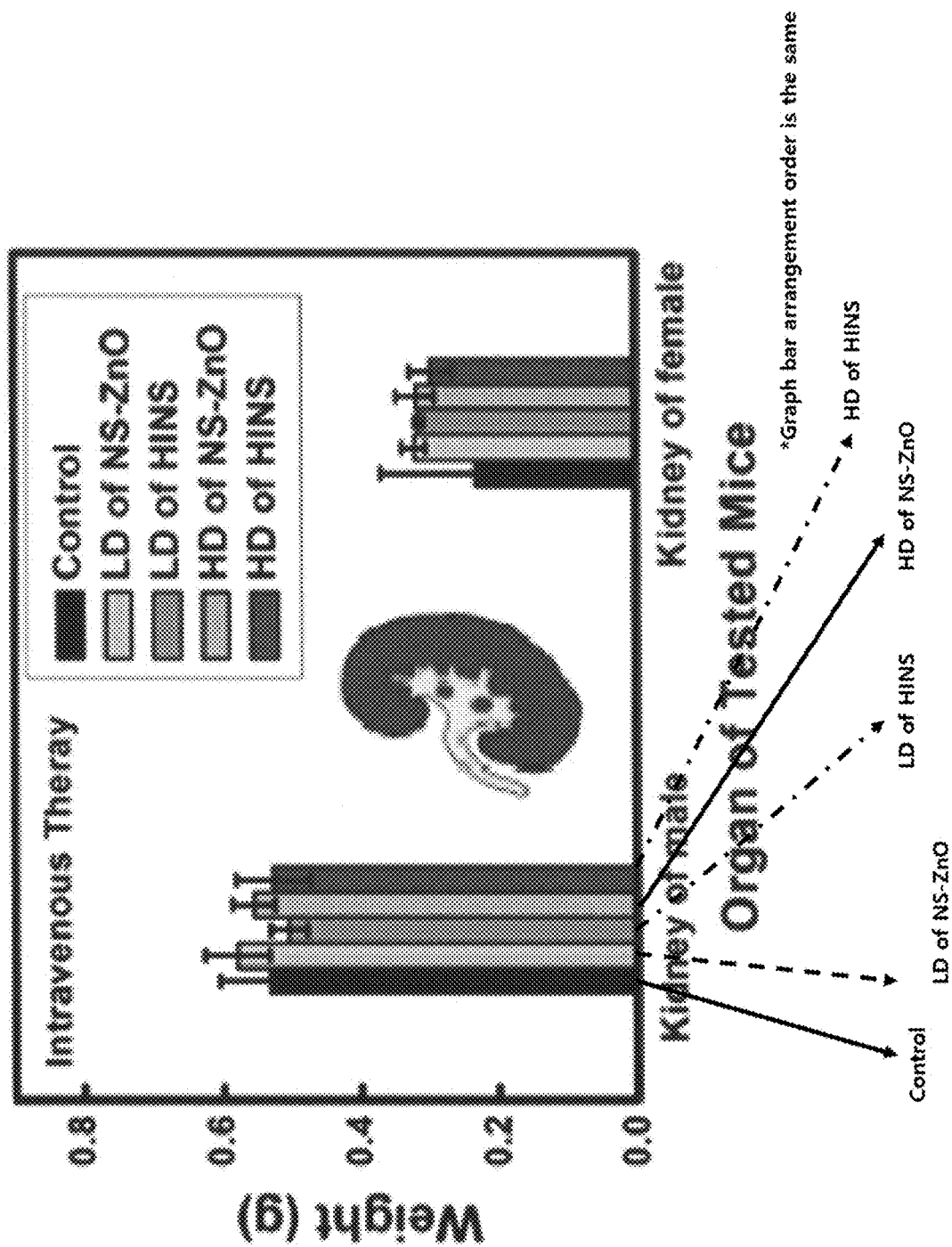
Figure 11D:
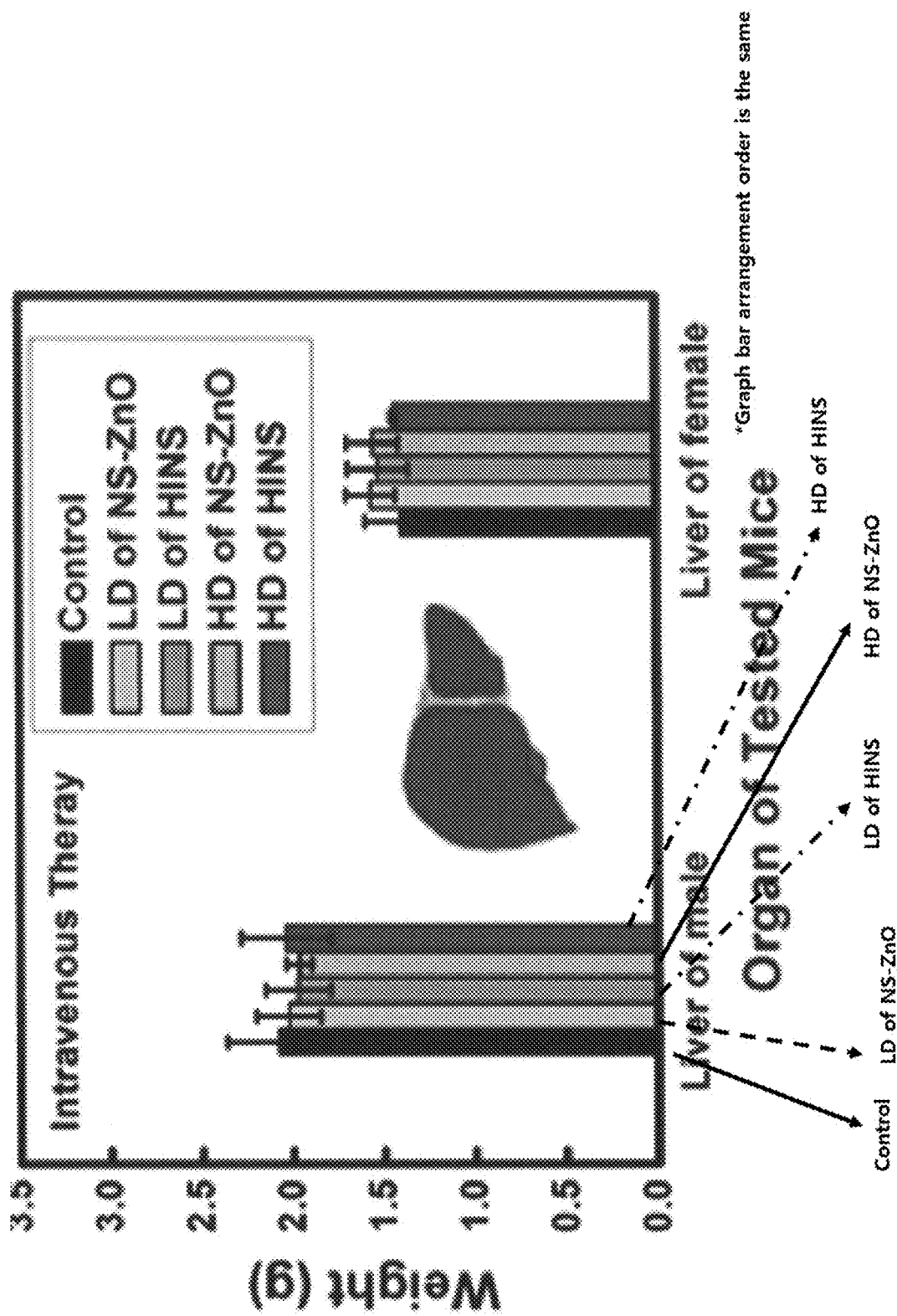
Figure 11E:
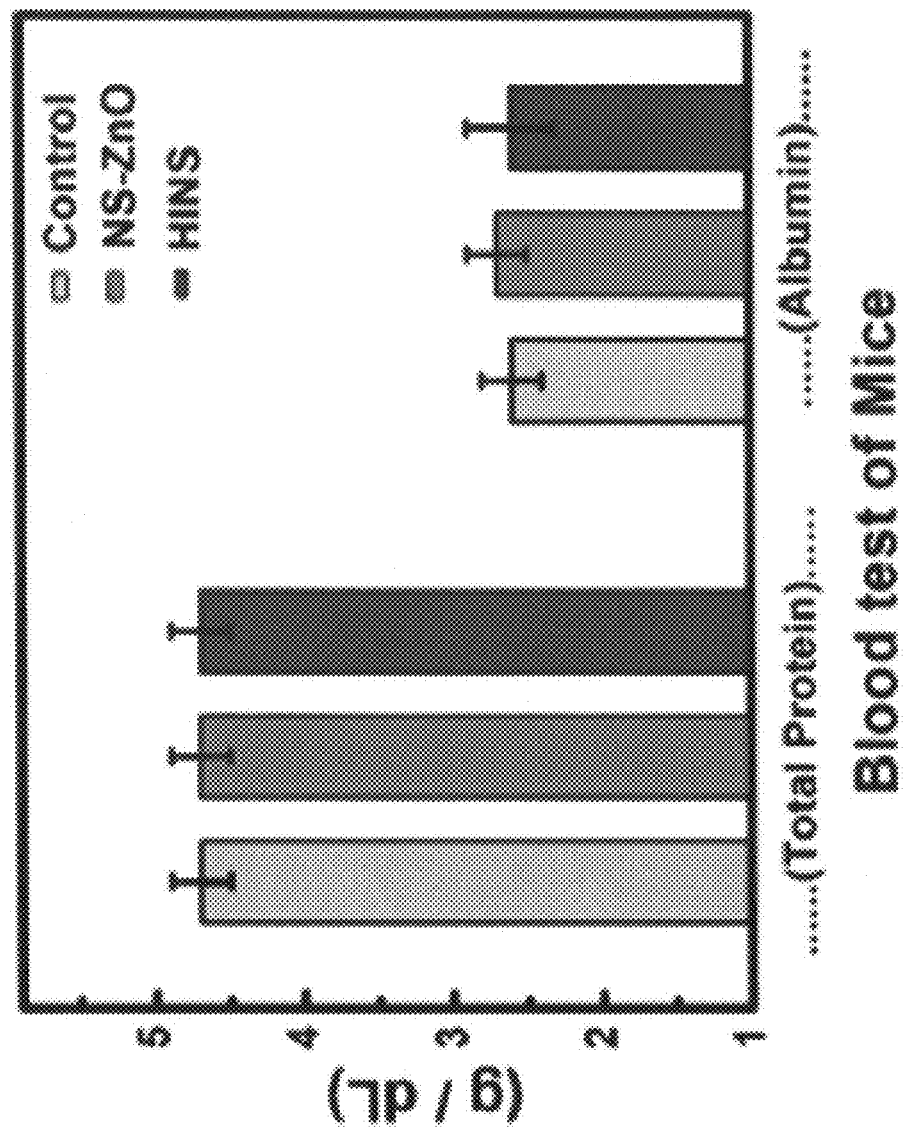
Figure 11F:
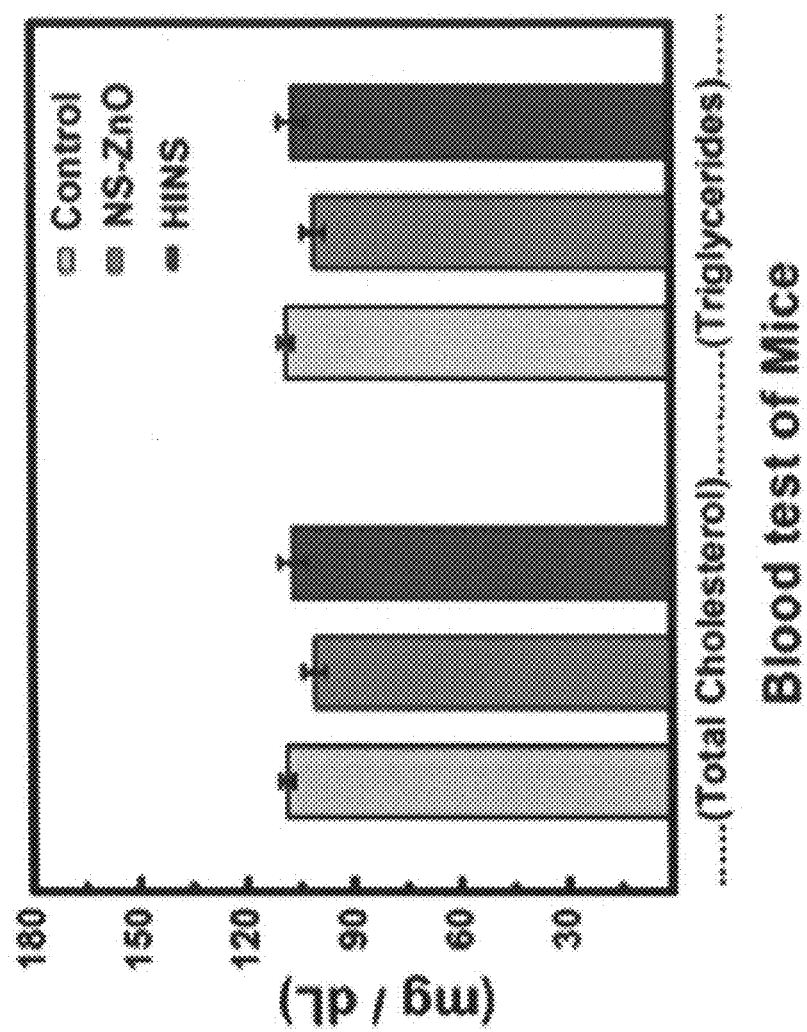

According to FIG. 10A, fresh sheep blood was used, HI-modified ZnO nanomaterials were added to the blood, and the tube was allowed to stand for 10 minutes. The HINS composite in the right tube was precipitated, whereas the left tube was ambiguous, this lack of such a clear precipitate indicates that ZnO NP—HI can fuse with blood cells to cause cytotoxicity and thrombi. The mixture was allowed to pass through a thin flexible fluid chip (length: 45 cm, volume: 350 µL) and the amount of ZnO in the discharged material was confirmed by UV-visible light spectroscopy. Since the slowest velocity of human blood is approximately 7 cm/s, the pump was set to a lower flow rate of 1 cm/s than the velocity, and the collected data is illustrated in FIG. 10B. From FIG. 10B, it can be seen that the HINS composite system had less ZnO loss than the ZnO NP—HI system. It can be seen that HI modification helps the HINS composite to move more smoothly in plasma, and the form thereof helps the HINS composite to lower flow resistance and flow more flexibly. From FIG. 10C, it can be confirmed that a large amount of ZnO NP—HI adhered to blood cells, but from FIG. 10D, it can be confirmed that the HINS composite is in a very excellent state.

From the above results, it can be seen that the HINS composite has excellent biocompatibility and can be used for intravenous administration because the HINS composite allows protein activity in blood to be maintained and does not cause thrombi.

[Test Example 5] In Vivo Toxicity and Biocompatibility Test

After intravenous injection of ZnO, toxic clinical indicators including tremor, spasms, salivation, nausea, vomiting, diarrhea, body weight changes, and death were observed daily in all animals for 14 days. There was no death in all experiments. There was no significance in body weight change or any toxic symptoms in both low dose (LD) ZnO NS—HI (DMP) and high dose (HD) ZnO NS—HI (DMP) groups. After 14 days, the animals were sacrificed, major organs including the brain, heart, lungs, spleen, testis or uterus were collected and weighed separately for males and females, and the results are illustrated on FIGS. 11A to 11F. Referring to FIGS. 11A to 11F, there was no difference between ZnO NS—HI (DMP) and the control. Furthermore, as a blood test result, the liver [damage signal: alanine aminotransferase (ALT) and bilirubin (T-Bili) release in blood] and the kidney [damage signal: urea nitrogen (BUN) and creatinine (crea) release in blood] were found to work well. Through the in vivo experimental results, the excellent biocompatibility of ZnO NS—HI (DMP) was verified in mice.

Although the present invention has been described above with reference to preferred exemplary embodiments of the present invention, a person with ordinary skill in the art can understand that the present invention can be modified and changed in various ways in a range not departing from the spirit and scope of the present invention described in the following claims.

What is claimed is:

1. A modified zinc oxide nanocomposite comprising zinc oxide nanocrystals modified with a compound represented by the following Chemical Formula 1:

[Chemical Formula 1]

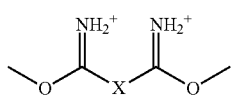

wherein, in Chemical Formula 1, X is $(CH_2)_n$, and n is an integer from 5 to 10, wherein the modified zinc oxide nanocomposite is prepared by mixing a salt of the compound represented by Chemical Formula 1 with the zinc oxide nanocrystals in a manner sufficient to provide for modified zinc oxide nanocrystals, wherein the zinc oxide nanocrystals are crystals having a spindle shape.

2. The modified zinc oxide nanocomposite of claim 1, wherein n is 5 or 6.

3. The modified zinc oxide nanocomposite of claim 1, wherein the zinc oxide nanocrystals have a size of 100 to 300 nm.

4. The modified zinc oxide nanocomposite of claim 1, wherein the modified zinc oxide nanocomposite exhibits a positive surface charge.

5. An antibiotic composition comprising the modified zinc oxide nanocomposite of claim 1 as an active ingredient.

6. The antibiotic composition of claim 5, wherein the antibiotic composition has antiviral, antibacterial or antifungal activity.

7. The antibiotic composition of claim 6, wherein the antibiotic composition has antibacterial activity against Gram-negative bacteria.

8. The antibiotic composition of claim 7, wherein the antibiotic composition has antibacterial activity against *Escherichia coli* or *Salmonella*.

9. The antibiotic composition of claim 5, wherein the antibiotic composition has antifungal activity against fungi of the genus *Aspergillus*.

10. The antibiotic composition of claim 5, wherein the antibiotic composition further comprises an additional antifungal agent.

11. A method of preventing contamination or infection by viruses, bacteria or fungi, inhibiting the growth of viruses, bacteria or fungi, or treating infections by viruses, bacteria or fungi comprising administering the antibiotic composition of claim 5 to a subject.

12. The method of claim 11, wherein the antibiotic composition is administered via injection.

13. An antifungal combination preparation containing the modified zinc oxide nanocomposite of claim 1 and an antifungal agent.

14. The antifungal combination preparation of claim 13, wherein the antifungal agent is itraconazole or amphotericin B.

15. A method of preventing contamination or infection by viruses, bacteria or fungi, inhibiting the growth of viruses, bacteria or fungi, or treating infections by viruses, bacteria or fungi comprising administering the antibiotic composition of claim 10 to a subject.

16. The method of claim 15, wherein the antibiotic composition is administered via injection.

* * * * *